United States Patent
Vicogne et al.

(10) Patent No.: US 10,435,450 B2
(45) Date of Patent: Oct. 8, 2019

(54) MET RECEPTOR AGONIST PROTEINS

(71) Applicants: CENTRE NATIONAL DE LA RECHERCHE SCIENTIFIQUE, Paris (FR); INSTITUT PASTEUR DE LILLE, Lille (FR); UNIVERSITA' DEGLI STUDI DI PAVIA, Pavia (IT); UNIVERSITÉ DE LILLE, Lille (FR)

(72) Inventors: Jerome Vicogne, Perenchies (FR); Oleg Melnyk, Annoeullin (FR); Nathalie Ollivier, Roubaix (FR); Eric Adriaenssens, Faumont (FR); Berenice Leclercq, Wasquehal (FR); Claire Simonneau, Jaunay-Clan (FR); Giovanni De Nola, Pavia (IT); Ermanno Gherardi, Pavia (IT); Hugo De Jonge, Pavia (IT)

(73) Assignees: CENTRE NATIONAL DE LA RECHERCHE SCIENTIFIQUE, Paris (FR); INSTITUT PASTEUR DE LILLE, Lille (FR); UNIVERSITA' DEGLI STUDI DI PAVIA, Pavia (IT); UNIVERSITÉ DE LILLE, Lille (FR)

( * ) Notice: Subject to any disclaimer, the term of this patent is extended or adjusted under 35 U.S.C. 154(b) by 0 days.

(21) Appl. No.: 15/544,710

(22) PCT Filed: Jan. 21, 2016

(86) PCT No.: PCT/EP2016/051267
§ 371 (c)(1),
(2) Date: Jul. 19, 2017

(87) PCT Pub. No.: WO2016/116577
PCT Pub. Date: Jul. 28, 2016

(65) Prior Publication Data
US 2017/0369545 A1   Dec. 28, 2017

(30) Foreign Application Priority Data
Jan. 21, 2015 (EP) .................... 15152027

(51) Int. Cl.
C07K 14/475 (2006.01)
C12N 15/63 (2006.01)
A61K 38/18 (2006.01)
A61K 38/00 (2006.01)

(52) U.S. Cl.
CPC ...... *C07K 14/4753* (2013.01); *A61K 38/1833* (2013.01); *C12N 15/63* (2013.01); *A61K 38/00* (2013.01); *C07K 2319/75* (2013.01)

(58) Field of Classification Search
None
See application file for complete search history.

(56) References Cited

U.S. PATENT DOCUMENTS

| 7,179,786 B2 | 2/2007 | Gherardi et al. |
| 2006/0003931 A1 | 1/2006 | Eigenbrot, Jr. et al. |
| 2009/0215686 A1 | 8/2009 | Xu et al. |

FOREIGN PATENT DOCUMENTS

| WO | 02/088354 A1 | 11/2002 |
| WO | 2009/093880 A2 | 7/2009 |
| WO | 2009/125986 A2 | 10/2009 |
| WO | 2011103382 A2 | 8/2011 |
| WO | 2011116396 A2 | 9/2011 |
| WO | 2013/065913 A1 | 5/2013 |

OTHER PUBLICATIONS

Sakata, H., et al., "Heparin Binding and Oligomerization of Hepatocyte Growth Factor/Scatter Factor Isoforms," The Journal of Biological Chemistry, vol. 272, No. 14, 1997, pp. 9457-9463.
Raibaut, L., et al., "Total Synthesis of Biotinylated N Domain of Human Hepatocyte Growth Factor," Bioorganic & Medicinal Chemistry, vol. 21, 2013, pp. 3486-3494.
Simonneau, C., et al., "Semi-Synthesis of a HGF/SF Kringle One (K1) Domain Scaffold Generates a Potent In Vivo MET Recptor Agonist," Chemical Science, vol. 6, No. 3, 2015, pp. 2110-2121.
Nakamura, "Structure and Function of Hepatocyte Growth Factor," Progress in Growth Factor Research, vol. 3, 1991, pp. 67-85.
Holmes, O., et al., "Insights into the Structure/Function of Hepatocyte Growth Factor/Scatter Factor from Studies with Individual Domains," J. Mol. Biol., vol. 367, 2007, pp. 395-408.
Miyazawa, K., et al., "An Alternatively Processed mRNA Generated from Human Hepatocyte Growth Factor Gene," Eur J. Biochem., vol. 197, 1991, pp. 15-22.
Nakamura, T., et al., "Purification and Subunit Structure of Hepatocyte Growth Factor from Rat Platelets," FEBS Letters, vol. 224, No. 2, 1987, pp. 311-316.
Zarnegar, R., et al., "Purification and Biological Characterization of Human Hepatopoietin A, A Polypeptide Growth Factor for Hepatocytes," Cancer Research, vol. 49, 1989, pp. 3314-3320.
Stoker, M., et al., "Scatter Factor is a Fibroblast-Derived Modulator of Epithelial Cell Mobility," Nature, vol. 327, 1987, pages pp. 239-242.
Gherardi, E., et al., "Purification of Scatter Factor, A Fibroblast-Derived Basic Protein that Modulates Epithelial Interactions and Movement," Proc. Natl. Acad. Sci, vol. 86, 1989, pp. 5844-5848.
Bottaro, D., et al., "Identification of the Hepatocyte Growth Factor Receptor as the c-met Proto-Oncogene Product," Science, vol. 251, pp. 802-804.
Chirgadze D. et al., "Crystal Structure of the NK1 Fragment of HGF/SF Suggests a Novel Mode for Growth Factor Dimenzation and Receptor Binding," Nature Structural Biology, vol. 6, No. 1, 1999, pp. 72-79.

(Continued)

*Primary Examiner* — Marianne P Allen
(74) *Attorney, Agent, or Firm* — Young & Thompson

(57) ABSTRACT

Disclosed are proteins derived from the HGF/SF which are able to induce activation of the tyrosine kinase receptor MET and their uses, in particular to promote tissue regeneration. Further disclosed are nucleic acid molecules coding such protein, expression vectors containing such nucleic acid molecule, host cells containing such expression vectors, and related compositions.

16 Claims, 23 Drawing Sheets

Figure 1:
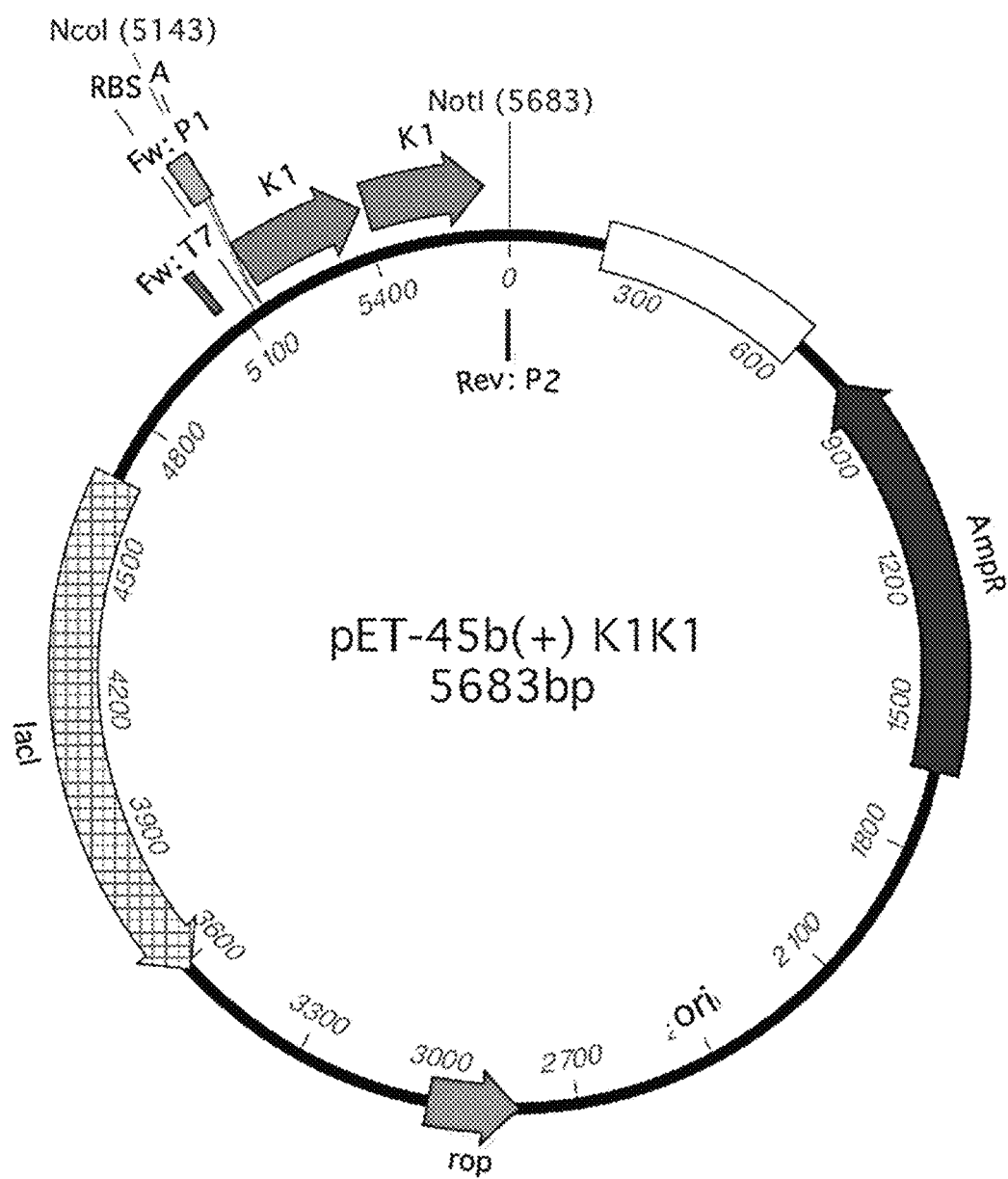

Specification includes a Sequence Listing.

(56) References Cited

OTHER PUBLICATIONS

Gherardi, E., et al., "Structural Basis of Hepatocyte Growth Factor/Scatter Factor and MET Signaling," PNAS, vol. 103, No. 11, 2006, pp. 4046-4051.
Stamos, J., et al., "Crystal Structure of the HGF β-Chain in Complex with the Sema Domain of the MET Receptor," The EMBO Journal, vol. 23, 2004, pp. 2325-2335.
Merkulova-Rainon, T., et al., "The N-Terminal Domain of Hepatocyte Growth Factor Inhibits the Angiogenic Behavior of Endothelial Cells Independently from Binding to the c-met Receptor," The Journal of Biological Chemistry, vol. 278, No. 39, 2003, pp. 37400-37408.
Huh, C., et al., "Hepatocyte Growth Factor / c-met Signaling Pathway is Required for Efficient Liver Regeneration and Repair," PNAS, vol. 101, No. 13, 2004, pp. 4477-4482.
Borowiak, M., et al., "Met Provides Essential Signals for Liver Regeneration," PNAS, vol. 101, No. 29, 2004, pp. 10608-10613.
Chmielowiec, J., et al., "c-Met is Essential for Wound Healing in the Skin," Journal of Cell Biology, vol. 177, No. 1, 2007, pp. 151-162.
Urbanek, K., et al., "Cardiac Stem Cells Possess Growth Factor-Receptor Systems that After Activation Regenerate the Infarcted Myocardium, Improving Ventricular Function and Long-Term Survival," Circulation Research, vol. 97, 2005, 68 pages.
Sun, W., et al., "Overexpression of HGF Retards Disease Progression and Prolongs Life Span in a Transgenic Mouse Model of ALS," The Journal of Neuroscience, vol. 22, No. 15, 2002, pp. 6537-6548.
Bai, L., et al., "Hepatocyte Growth Factor Mediates MSCs Stimulated Functional Recovery in Animal Models of MS," Nat. Neuroscience, vol. 15, No. 6, pp. 862-870.
Birchmeir, et al., "Met, Metastasis, Motility, and More," Nature Reviews, Molecular Cell Biology, vol. 4, 2003, pp. 915-925.
Ross, J., et al., "Protein Engineered Variants of Hepatocyte Growth Factor/Scatter Factor Promote Proliferation of Primary Human Hepatocytes and in Rodent Liver," Gastroenterology, vol. 142, 2012, pp. 897-906.
Roos, F., et al., "Induction of Liver Growth in Normal Mice by Infusion of Hepatocyte Growth Factor/Scatter Factor," The Journal of Physiology, 1995, pp. G380-G386.
Hartmann, G., et al., "Engineered Mutants of HGF/SF with Reduced Binding to Heparan Sulphate Proteoglycans, Decreased Clearance and Enhanced Activity," Current Biology, vol. 8, No. 3, 1997, pp. 125-134.
Yang, Z., et al., "Improvement of Heart Function in Postinfarct Heart Failure Swine Models After Hepatocyte Growth Factor Gene Transfer: Comparison of Low-, Medium- and High-Dose Groups," Mol. Biol. Rep., vol. 37, 2010, pp. 2075-2081.
Lietha, D., et al., "Crystal Structures of NK1-Heparin Complexes Reveal the Basis for NK1 Activity and Enable Engineering of Potent Agonists of the MET Receptor," The EMBO Journal, vol. 20, No. 20, 2001, pp. 5543-5555.
Smith, T., et al., "Identification of Common Molecular Subsequences," J. Mol. Biol., vol. 147, 1981, pp. 195-197.
Liu, C., et al., "An Engineered Dimeric Fragment of Hepatocyte Growth Factor is a Potent c-MET Agonist," FEBS Letters, vol. 588, No. 24, 2014, pp. 4831-4837.
Ancot, F., et al., "Shedding-Generated Met Receptor Fragments Can Be Routed to Either the Proteasomal or the Lysosomal Degradation Pathway," Traffic, vol. 13, No. 9, 2012, pp. 1261-1272.
International Search Report issued in Application No. PCT/EP2016/051267, dated Mar. 10, 2016.
European Search Report issued in Application No. EP 15 15 2027, dated Jul. 2, 2015.

X100

X40

X100

X40

X100

A

B

RMSD : 0.819 Å

MET RECEPTOR AGONIST PROTEINS

The present invention relates to proteins comprising two K1 domains from the Hepatocyte Growth Factor/Scatter Factor (HGF/SF).

Hepatocyte growth factor/scatter factor (HGF/SF) is a secreted 90 kDa protein with a complex domain structure which is synthesised as an inactive precursor and is subsequently converted proteolytically to a two-chain (α/β) active species (Nakamura, T., Structure and function of hepatocyte growth factor. *Prog Growth Factor Res* 3, 67-85 (1991); Holmes et al., Insights into the structure/function of hepatocyte growth factor/scatter factor from studies with individual domains. *Mol Biol* 367, 395-408 (2007)). The α chain consists of an N terminal domain (N) and four copies of the kringle domain (K1, K2, K3 and K4). The β chain is a catalytically inactive serine proteinase homology domain (SPH). Two receptor binding sites have been identified in HGF/SF: a high-affinity site located in the N-terminal region of the a chain and a low-affinity site located in the β chain.

HGF/SF is a potent growth and motility factor discovered independently as a liver mitogen (hepatocyte growth factor, HGF) (Miyazawa et al., Molecular cloning and sequence analysis of cDNA for human hepatocyte growth factor. *Biochem Biophys Res Commun* 163, 967-973 (1989); Nakamura et al., Purification and subunit structure of hepatocyte growth factor from rat platelets. *FEBS Lett* 224, 311-316 (1998); Zarnegar et al., Purification and biological characterization of human hepatopoietin a, a polypeptide growth factor for hepatocytes. *Cancer Res* 49, 3314-3320 (1989)) and a fibroblast-derived, epithelial motility factor (scatter factor, SF) (Stoker et al., Scatter factor is a fibroblast-derived modulator of epithelial cell mobility. *Nature* 327, 239-242 (1987); Gherardi et al., Purification of scatter factor, a fibroblast-derived basic protein that modulates epithelial interactions and movement. *Proc Natl Acad Sci USA* 86, 5844-5848 (1989)). A receptor tyrosine kinase MET encoded by a proto-oncogene was subsequently demonstrated to be the receptor for HGF/SF (Bottaro et al., Identification of the hepatocyte growth factor as the c-met proto-oncogene product. *Science* 251, 802-804 (1991)).

Interestingly, the primary HGF/SF transcript encodes two alternative splice variants. The first variant is caused by a premature translation termination and generates the NK1 protein containing the N domain and the first Kringle domain (K1) of HGF/SF. NK1 protein possesses a marked agonist activity but requires heparan sulfate interaction to induce complete MET activation. Structurally, NK1 protein consists of two globular domains that, in the presence of heparin, form a "head to tail" homodimer probably responsible for the MET dimerisation and activation (Chirgadze et al., Crystal structure of the NK1 fragment of HGF/SF suggests a novel mode for growth factor dimerization and receptor binding. *Nat Struct Biol* 6, 72-79 (1999). The second splice variant, also generated by a premature termination, produces the NK2 protein, containing the N domain and the first two kringle domains. NK2 is considered as a natural MET antagonist. Indeed, NK2 maintains its MET binding capacity, but due to its conformational properties, lacks the ability to activate MET. However, structure-based targeted mutations allow NK2 to be efficiently switched from MET antagonist to agonist by repositioning the K1 domain in a conformation close to that of NK1.

Beside many attempts to propose a unified and convergent interaction model, the MET binding mechanisms of HGF/SF are still unclear and controversial. In particular, no crystal structure of NK1 in complex with a soluble MET extracellular domain is yet available. HGF/SF is a bivalent ligand that contains a high and low affiny binding sites for MET located respectively in the N-terminal region of the α-chain (N and/or K1 domains) and in the β-chain (SPH domain). Binding of HGF/SF to the MET ectodomain in solution yields complexes with 2:2 stoichiometry (Gherardi et al., Structural basis of hepatocyte growth factor/scatter factor and met signalling. *Proc Natl Acad Sci USA* 103, 4046-4051 (2006)). The SPH domain binds MET with a well-defined interface. However, the localisation of NK1 binding site on MET is still unclear, and the exact HGF/SF-MET interaction model remains controversial (Holmes et al., Insights into the structure/function of hepatocyte growth factor/scatter factor from studies with individual domains. *J Mol Biol* 367, 395-408 (2007); Stamos et al., Crystal structure of the HGF beta-chain in complex with the sema domain of the met receptor. *The EMBO Journal* 23, 2325-2335 (2004); Merkulova-Rainon et al., The N-terminal domain of hepatocyte growth factor inhibits the angiogenic behavior of endothelial cells independently from binding to the c-Met-receptor. *J Biol Chem* 278, 37400-37408 (2003)).

HGF/SF and MET play essential physiological roles both in development and in tissue/organ regeneration. In particular, HGF/SF-MET is essential for liver and skin regeneration after hepatectomy (Huh et al., Hepatocyte growth factor/c-met signaling pathway is required for efficient liver regeneration and repair. *Proc Natl Acad Sci USA* 101, 4477-4482 (2004); Borowiak et al., Met provides essential signals for liver regeneration. *Proc Natl Acad Sci USA* 101, 10608-10613 (2004)) and skin wounds (Chmielowiec et al., C-met is essential for wound healing in the skin. *J Cell Biol* 177, 151-162 (2007)). HGF/SF further protects cardiac and skeletal muscle from experimental damage (Urbanek et al., Cardiac stem cells possess growth factor-receptor systems that after activation regenerate the infarcted myocardium, improving ventricular function and long-term survival. *Circ Res* 97, 663-673 (2005)), delays progression of a transgenic model of motor neuron disease (Sun et al., Overexpression of HGF retards disease progression and prolongs life span in a transgenic mouse model of ALS. *J Neurosci* 22, 6537-6548 (2002)) and an immunological model of multiple sclerosis (Bai et al., Hepatocyte growth factor mediates mesenchymal stem cell-induced recovery in multiple sclerosis models. *Nature neuroscience* 15, 862-870 (2012)). Together, these studies highlight a vast potential of HGF/SF in regenerative medicine, a concept supported by a number of pre-clinical and more recent clinical studies.

In particular, many investigations are concentrating on HGF/SF agonist synthesis to allow tissue regeneration, especially for liver regeneration after hepatectomy or lesions involved in diabetes diseases.

Since the current knowledge of the HGF/SF-MET interactions does not allow the rational design of HGF/SF-MET agonists, the usefulness of HGF/SF has been established using native HGF/SF, gene delivery methods and NK1-based MET agonists.

However, native HGF/SF is a protein with limited tissue diffusion reflecting its role as a locally-acting tissue morphogen (Birchmeier et al., Met, metastasis, mobility and more. *Nat Rev Mol Cell Biol* 4, 915-925 (2003); Ross et al., Protein Engineered Variants of Hepatocyte Growth Factor/Scatter Factor Promote Proliferation of Primary Human Hepatocytes and in Rodent Liver. *Gastroenterology* 142, 897-906 (2012)). Indeed, after local or systemic administration, HGF/SF is immobilized by heparan sulfate present in the extracellular matrix, resulting in a severely decreased diffusion towards MET receptors in more distant tissues (Roos et al., Induction of liver growth in normal mice by infusion of hepatocyte growth factor/scatter factor. *The American Journal of Physiology* 268, G380-386 (1995); Hartmann et al., Engineered mutants of HGF/SF with reduced binding to heparan sulfate proteoglycans, decreased clearance and enhanced activity in vivo. *Curr Biol* 8, 125-134 (1998)). Moreover, native HGF/SH is also difficult and very costly to produce owing to its complex, multidomain structure.

Gene delivery methods, including intramuscular injection of naked DNA encoding HGF/SF addresses several of the problems associated with the use of native HGF/SF as a protein therapeutic (the cost of production of the HGF/SF protein, for example). Clinical trials with HGF/SF DNA are currently conducted in patients with diabetic peripheral neuropathy and in patients with amyotrophic lateral sclerosis. The results of these studies are awaited with interest but there remain limitations with the current gene delivery methods in terms of the achievement of stable therapeutic levels of the gene products and the relative availability to specific tissue domains and organs due to limited diffusion. For example, such gene delivery methods are based on plasmid delivery systems (patent applications WO 2009/093880, WO 2009/125986 and WO 2013/065913) or adenovirus-based delivery systems (Yang et al., Improvement of heart function in postinfarct heart failure swine models after hepatocyte growth factor gene transfer: comparison of low-, medium- and high-doses groups. *Mol Biol Rep* 37, 2075-2081 (2010)).

Currently available NK1-based MET agonists, such as 1K1 (i.e. a NK1 mutant), have a strong agonistic activity and offer advantages over HGF/SF (Lietha et al., Crystal structures of NK1-heparin complexes reveal the basis for NK1 activity and enable engineering of potent agonists of the MET receptor. *The EMBO journal* 20, 5543-5555 (2001) and U.S. Pat. No. 7,179,786). Unlike native HGF/SF, this NK1 mutant can be effectively produced in heterologous expression systems, is stable in physiological buffers and thus can be administered with full control over dosage and plasma concentration. However, a potential limitation of NK1 is its strong residual affinity for heparan sulfate that avoids tissue diffusion.

Therefore, there is a need for potent MET agonists with an improved stability, an improved shelf life, an optimal bioavailability, and that can be produced at low cost and easily administered.

One of the aims of the invention is to provide a protein able to induce activation of the tyrosine kinase receptor MET.

Another aim of the invention is also to provide compositions containing said protein.

Another aim of the invention further relates to the use of said protein, in particular for diagnostical and therapeutical applications.

The present invention relates to a protein containing two peptide domains, named $K1_a$ and $K1_b$ respectively, each of said peptide domains $K1_a$ and $K1_b$ comprising a K1 peptide domain (Kringle 1) of the Hepatocyte Growth Factor/Scatter Factor (HGF/SF),
said K1 peptide domain consisting of a sequence with at least 80% identity, preferably at least 90% identity, to SEQ ID NO: 1,
said protein being able to induce activation of the tyrosine kinase receptor MET.

The present application is based on the unexpected two-pronged observation made by the Inventors that K1 domain constitutes the building block for potent MET agonists and that it is possible to engineer K1 dimers with a potent MET agonist activity.

In the invention, the expressions "$K1_a$" and "$K1_b$" all refer to a peptide sequence comprising the K1 domain of HGF/SF.

The protein of the invention is a covalent dimer of the K1 domain of HGF/SF, i.e. two K1 domains are covalently linked to each other by an amino acid chain. The protein of the invention may be designated by the expression "K1K1".

In particular, the invention relates to a protein containing two peptide domains, named $K1_a$ and $K1_b$ respectively, each of said peptide domains $K1_a$ and $K1_b$ comprising a K1 peptide domain (Kringle 1) of the Hepatocyte Growth Factor/Scatter Factor (HGF/SF), said K1 peptide domain consisting of a sequence with at least 80% identity, preferably at least 90% identity, to SEQ ID NO: 1,
said protein being able to induce activation of the tyrosine kinase receptor MET,
with the proviso that said protein does not comprise the N-terminal domain of HGF/SF.

The protein of the invention has many technical and financial advantages.

The most important technical advantage is that the protein of the invention has a potent MET agonistic activity. Thus, this protein is able to activate the MET receptor and/or induce any phenotype associated to the MET activation in various in vitro and in vivo assays.

The protein has a MET agonistic activity if it is able to:
bind to the MET receptor,
activate the MET phosphorylation and the downstream signaling in cells, and
induce at least one cellular phenotype such as survival, proliferation, morphogenesis and/or migration.

The validation of these criteria can be shown using protein-protein interaction tests (such as SPR (Surface Plasmon Resonance), AlphaScreen, Pull-Down technique or gel-filtration chromatography), phosphorylation tests (such as western-blot, ELISA or AlphaScreen) and phenotypic tests (such as scattering, MTT assay or Matrigel™ induced morphogenesis).

For example, MET activation and downstream signaling in cells can be analyzed in vitro by western blot and quantified by homogeneous time resolved fluorescence (HTRF) approaches. In vivo, it is also possible to analyze local angiogenesis and protection of mice from Fas-induced fulminant hepatitis.

Another technical advantage is that the protein of the invention can be administered with full control over dosage and/or plasma concentration.

Moreover, one of the major disadvantages of native HGF/SF is the fact that it strongly binds to heparan sulfate in the extracellular matrix. This severely limits the diffusion of the molecule to more distant sites. The protein of the invention in contrast is missing the high affinity heparan sulfate site.

Therefore, the protein is not immobilized by heparan sulfate chains of extracellular matrix, contrary to HGF/SF. Therefore, when injected into a patient, the protein of the invention can diffuse from the area of injection towards MET receptors in distant tissues, whereas native HGF/SF is unable to do. This is demonstrated by in vivo experiments in mice. However, the presence of a low-affinity heparin binding site in the kringle domain allows efficient purification through heparin-sepharose affinity chromatography.

Some of the financial advantages are that the protein of the invention can be easily produced in large amounts at low cost. Indeed, the protein can be recombinantly produced in host cells used as expression systems, such as bacteria or yeasts.

In an embodiment, the present invention relates to a protein containing two peptide domains of 70 to 100 amino acids, named $K1_a$ and $K1_b$ respectively, each of said peptide domains $K1_a$ and $K1_b$ comprising a K1 peptide domain (Kringle 1) of the Hepatocyte Growth Factor/Scatter Factor (HGF/SF),
said K1 peptide domain consisting of a sequence with at least 80% identity, preferably at least 90% identity, to SEQ ID NO: 1,
said protein being able to induce activation of the tyrosine kinase receptor MET.

In an embodiment, the present invention relates to a protein containing two peptide domains of 70 to 100 amino acids, named $K1_a$ and $K1_b$ respectively, each of said peptide domains $K1_a$ and $K1_b$ comprising a K1 peptide domain (Kringle 1) of the Hepatocyte Growth Factor/Scatter Factor (HGF/SF),
said K1 peptide domain consisting of a sequence with at least 80% identity, preferably at least 90% identity, to SEQ ID NO: 2,
said protein being able to induce activation of the tyrosine kinase receptor MET.

In an embodiment, the present invention relates to a protein containing two peptide domains, named $K1_a$ and $K1_b$ respectively, each of said peptide domains $K1_a$ and $K1_b$ comprising or consisting of a sequence of 70 to 100 amino acids with at least 80% identity, preferably at least 90% identity to SEQ ID NO: 1,
said protein being able to induce activation of the tyrosine kinase receptor MET.

In one embodiment, the invention relates to a protein as defined above, wherein the size of each of said peptide domains K1a and K1b is at least 70 amino acids, preferably at least 74 amino acids, more preferably at least 79 amino acids.

In particular, the size of $K1_a$ and/or $K1_b$ is 70 to 100 amino acids. Such a K1 peptide domain can consist of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acids.

In one embodiment, the invention relates to a protein as defined above, wherein peptide domains $K1_a$ and $K1_b$ are identical.

In one embodiment, the invention relates to a protein as defined above, wherein peptide domains $K1_a$ and $K1_b$ are different from each other.

In one embodiment, the invention relates to a protein as defined above, wherein each of peptide domains $K1_a$ and $K1_b$ consists of an amino acid sequence SEQ ID NO: 1.

In one embodiment, the invention relates to a protein as defined above, wherein each of peptide domains $K1_a$ and $K1_b$ consists of an amino acid sequence SEQ ID NO: 2.

In one embodiment, the invention relates to a protein as defined above, wherein each of peptide domains $K1_a$ and $K1_b$ consists of an amino acid sequence chosen among the amino sequences SEQ ID NO: 1 and SEQ ID NO: 2.

In one embodiment, the present invention relates to a protein as defined above, wherein said peptide domains $K1_a$ and/or $K1_b$ comprise at least one addition, deletion or substitution of an amino acid relative to SEQ ID NO: 1, the K1 peptide domains of $K1_a$ and $K1_b$ consisting of a sequence with at least 80% identity to SEQ ID NO: 1.

In one embodiment, the present invention relates to a protein as defined above, wherein said peptide domains $K1_a$ and/or $K1_b$ comprise at least one substitution of the amino acid K in position 5 and/or the amino acid R in position 7 relative to SEQ ID NO: 1, the K1 peptide domains of $K1_a$ and $K1_b$ consisting of a sequence with at least 80% identity to SEQ ID NO: 1.

In one embodiment, the present invention relates to a protein as defined above, wherein said peptide domains $K1_a$ and/or $K1_b$ comprise at least one substitution chosen among K5E and R7E relative to SEQ ID NO: 1, the K1 peptide domains of $K1_a$ and $K1_b$ consisting of a sequence with at least 80% identity to SEQ ID NO: 1.

In one embodiment, the present invention relates to a protein as defined above, wherein each of said peptide domains $K1_a$ and $K1_b$ comprise the substitutions K5E and R7E relative to SEQ ID NO: 1, each K1 peptide domain consisting of a sequence with at least 80% identity to SEQ ID NO: 1.

SEQ ID NO: 1 corresponds to the sequence of the human K1 domain, i.e. the region from the amino acid in position 128 to the amino acid position 206 of HGF/SF represented by SEQ ID NO: 12.

SEQ ID NO: 1 has a size of 79 amino acids and is flanked by two cysteines.

SEQ ID NO: 2 corresponds to the variant of the human K1 domain in which 5 amino acids are missing.

TABLE 1

| | Sequences of HGF/SF and K1 domains. |
|---|---|
| SEQ ID NO: 1 | CIIGKGRSYKGTVSITKSGIKCQPWSSMIPHEH<u>SFLPS</u>SYRGK DLQENYCRNPRGEEGGPWCFTSNPEVRYEVCDIPQC |
| SEQ ID NO: 2 | CIIGKGRSYKGTVSITKSGIKCQPWSSMIPHEHSYRGKDLQEN YCRNPRGEEGGPWCFTSNPEVRYEVCDIPQC |
| SEQ ID NO: 12 | MWVTKLLPALLLQHVLLHLLLLPIAIPYAEGQRKRRNTIHEF KKSAKTTLIKIDPALKIKTKKVNTADQCANRCTRNKGLPFTC KAFVFDKARKQCLWFPFNSMSSGVKKEFGHEFDLYENKDYI RNCIIGKGRSYKGTVSITKSGIKCQPWSSMIPHEHSFLPSSYR GKDLQENYCRNPRGEEGGPWCFTSNPEVRYEVCDIPQCSEV ECMTCNGESYRGLMDHTESGKICQRWDHQTPHRHKFLPER YPDKGFDDNYCRNPDGQPRPWCYTLDPHTRWEYCAIKTCA DNTMNDTDVPLETTECIQGQGEGYRGTVNTIWNGIPCQRWD SQYPHEHDMTPENFKCKDLRENYCRNPDGSESPWCFTTDPN IRVGYCSQIPNCDMSHGQDCYRGNGKNYMGNLSQTRSGLT CSMWDKNMEDLHRHIFWEPDASKLNENYCRNPDDDAHGP WCYTGNPLIPWDYCPISRCEGDTTPTIVNLDHPVISCAKTKQ LRVVNGIPTRTNIGWMVSLRYRNKHICGGSLIKESWVLTAR QCFPSRDLKDYEAWLGIHDVHGRGDEKCKQVLNVSQLVYG PEGSDLVLMKLARPAVLDDFVSTIDLPNYGCTIPEKTSCSVY GWGYTGLINYDGLLRVAHLYIMGNEKCSQHHRGKVTLNES EICAGAEKIGSGPCEGDYGGPLVCEQHKMRMVLGVIVPGRG CAIPNRPGIFVRVAYYAKWIHKIILTYKVPQS |

The variant of the human K1 domain, represented by SEQ ID NO: 2, differs from the human K1 domain, represented by SEQ ID NO: 1, by a deletion of 5 consecutive amino acids: SFLPS.

$K1_a$ and $K1_b$ can consist of an amino acid sequence SEQ ID NO: 1 or of an amino acid sequence with at least 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 1.

The "percentage identity" between two peptide sequences, as defined in the present invention, is determined by comparing two sequences aligned optimally, through a window of comparison. The amino acid sequence in the comparison window may thus comprise additions or deletions (e.g. "gaps") relative to the reference sequence (which does not include these additions or deletions) so to obtain an optimal alignment between the two sequences.

The percentage identity is calculated by determining the number of positions in which an amino acid residue is identical in the two compared sequences and dividing this number by the total number of positions in the window of comparison and multiplying the result by one hundred to obtain the percent identity of two amino acid sequences to each other. The percentage identity may be determined over the entire amino acid sequence or over selected domains, preferably over the entire amino acid sequence. For local alignments, the Smith-Waterman algorithm is particularly useful (Smith T F, Waterman M S (1981) J. Mol. Biol. 147(1); 195-7).

In one embodiment, the invention relates to a protein as defined above, wherein each of peptide domains K1$_a$ and K1$_b$ is encoded by a nucleic acid sequence chosen among the group consisting of SEQ ID NO: 3 and SEQ ID NO: 4.

SEQ ID NO: 3 corresponds to the nucleic acid sequence encoding the amino acid sequence SEQ ID NO: 1.

SEQ ID NO: 4 corresponds to the nucleic acid sequence encoding the amino acid sequence SEQ ID NO: 2.

TABLE 2

Nucleic acid sequences coding K1 domains.

| | |
|---|---|
| SEQ ID NO: 3 | TGCATCATTGGTAAAGGACGCAGCTACAAGGGAACAGTAT CTATCACTAAGAGTGGCATCAAATGTCAGCCCTGGAGTTC CATGATACCACACGAACACAGCTTTTTGCCTTCGAGCTATC GGGGTAAAGACCTACAGGAAAACTACTGTCGAAATCCTCG AGGGGAAGAAGGGGGACCCTGGTGTTTCACAAGCAATCCA GAGGTACGCTACGAGGTCTGTGACATTCCTCAGTGTT |
| SEQ ID NO: 4 | TGCATCATTGGTAAAGGACGCAGCTACAAGGGAACAGTAT CTATCACTAAGAGTGGCATCAAATGTCAGCCCTGGAGTTC CATGATACCACACGAACACAGCTATCGGGGTAAAGACCTA CAGGAAAACTACTGTCGAAATCCTCGAGGGGAAGAAGGG GGACCCTGGTGTTTCACAAGCAATCCAGAGGTACGCTACG AGGTCTGTGACATTCCTCAGTGTT |

In one embodiment, the invention relates to a protein as defined above, said protein comprising a peptide linker connecting K1$_a$ and K1$_b$.

The present invention relates to a protein consisting of two peptide domains, named K1$_a$ and K1$_b$ respectively, connected to each other by a peptide linker, each of said peptide domains K1$_a$ and K1$_b$ comprising a K1 peptide domain (Kringle 1) of the Hepatocyte Growth Factor/Scatter Factor (HGF/SF), said K1 peptide domain consisting of a sequence with at least 80% identity, preferably at least 90% identity, to SEQ ID NO: 1, said protein being able to induce activation of the tyrosine kinase receptor MET.

In one embodiment, the invention relates to a protein as defined above, wherein said peptide linker is constituted by 1 to 50 amino acids, preferably from 10 to 20 amino acids.

In particular, the size of the linker is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids.

In an embodiment, the size of the linker is 4 amino acids.

In one embodiment, the invention relates to a protein as defined above, wherein said peptide linker comprises or consists of the amino acid sequence SEQ ID NO: 5 (SEVE).

The peptide linker SEQ ID NO: 5 can be encoded by the nucleic acid sequence SEQ ID NO: 6 (TCAGAAGTTGAA).

In one embodiment, the invention relates to a protein comprising or consisting of an amino acid sequence SEQ ID NO: 7 or an amino acid sequence with at least 80%, preferably 90% identity to SEQ ID NO: 7.

In one embodiment, the invention relates to a protein comprising or consisting of an amino acid sequence SEQ ID NO: 8 or an amino acid sequence with at least 80%, preferably 90% identity to SEQ ID NO: 8.

TABLE 3

Sequences of K1K1 proteins.

| | |
|---|---|
| SEQ ID NO: 7 | CIIGKGRSYKGTVSITKSGIKCQPWSSMIPHEHSFLPSSYRGK DLQENYCRNPRGEEGGPWCFTSNPEVRYEVCDIPQCSEVECII GKGRSYKGTVSITKSGIKCQPWSSMIPHEHSFLPSSYRGKDLQ ENYCRNPRGEEGGPWCFTSNPEVRYEVCDIPQC |
| SEQ ID NO: 8 | CIIGKGRSYKGTVSITKSGIKCQPWSSMIPHEHSYRGKDLQEN YCRNPRGEEGGPWCFTSNPEVRYEVCDIPQCSEVECIIGKGRS YKGTVSITKSGIKCQPWSSMIPHEHSYRGKDLQENYCRNPRG EEGGPWCFTSNPEVRYEVCDIPQC |

SEQ ID NO: 7 is constituted, from N-terminus to C-terminus, by SEQ ID NO: 1, SEQ ID NO: 6 and SEQ ID NO: 1.

SEQ ID NO: 8 is constituted, from N-terminus to C-terminus, by SEQ ID NO: 2, SEQ ID NO: 6 and SEQ ID NO: 2.

In an embodiment, the protein of the invention comprises a cleavable tag, such as a polyhistidine-tag at its N-terminal and/or C-terminal extremities. Such a polyhistidine-tag can be used to allow affinity purification of tagged proteins.

In one embodiment, the invention relates to a protein comprising or consisting of an amino acid sequence SEQ ID NO: 9.

TABLE 4

| Sequence of a C-terminally tagged K1K1 protein. | |
|---|---|
| SEQ ID NO: 9 | MAIRNCIIGKGRSYKGTVSITKSGIKCQPWSSMIPHEHSFLPS<br>SYRGKDLQENYCRNPRGEEGGPWCFTSNPEVRYEVCDIPQCSE<br>VECIIGKGRSYKGTVSITKSGIKCQPWSSMIPHEHSFLPSSYR<br>GKDLQENYCRNPRGEEGGPWCFTSNPEVRYEVCDIPQCSEVEH<br>HHHHH |

TABLE 5

| K1K1 variants. | |
|---|---|
| SEQ ID NO: 13 (tagless variant) Variant 1 | MAIRNCIIGKGRSYKGTVSITKSGIKCQPWSSMIPHEHSFL<br>PSSYRGKDLQENYCRNPRGEEGGPWCFTSNPEVRYEVCDIP<br>QCSEVECIIGKGRSYKGTVSITKSGIKCQPWSSMIPHEHSF<br>LPSSYRGKDLQENYCRNPRGEEGGPWCFTSNPEVRYEVCDI<br>PQCSEVE |
| SEQ ID NO: 14 (Long linker variant) Variant 2 | MAIRNCIIGKGRSYKGTVSITKSGIKCQPWSSMIPHEHSFL<br>PSSYRGKDLQENYCRNPRGEEGGPWCFTSNPEVRYEVCDIP<br>QCGGGGSLVPRGSGGGGSCIIGKGRSYKGTVSITKSGIKCQ<br>PWSSMIPHEHSFLPSSYRGKDLQENYCRNPRGEEGGPWCFT<br>SNPEVRYEVCDIPQCSEVE |
| SEQ ID NO: 15 (GS-linker variant) Variant 3 | MAIRNCIIGKGRSYKGTVSITKSGIKCQPWSSMIPHEHSFL<br>PSSYRGKDLQENYCRNPRGEEGGPWCFTSNPEVRYEVCDIP<br>QCGSGGCIIGKGRSYKGTVSITKSGIKCQPWSSMIPHEHSF<br>LPSSYRGKDLQENYCRNPRGEEGGPWCFTSNPEVRYEVCDI<br>PQCSEVE |

TABLE 5-continued

| K1K1 variants. | |
|---|---|
| SEQ ID NO: 16 (heparin mutant variant) Variant 4 | MAIRNCIIGEGESYKGTVSITKSGIKCQPWSSMIPHEHSFL<br>PSSYRGKDLQENYCRNPRGEEGGPWCFTSNPEVRYEVCDIP<br>QCSEVECIIGEGESYKGTVSITKSGIKCQPWSSMIPHEHSF<br>LPSSYRGKDLQENYCRNPRGEEGGPWCFTSNPEVRYEVCDI<br>PQCSEVEHHHHHH |

SEQ ID NO: 13 corresponds to a K1K1 protein with no histidine tag.

SEQ ID NO: 14 corresponds to a K1K1 protein of the invention wherein the SEVE linker has been replaced by a sequence of 16 aminoacids (GGGGSLVPRGSGGGGS, SEQ ID NO: 17) as a flexible linker. This elongated linker contains a cleavage site for thrombin (LVPRGS, SEQ ID NO: 18) allowing separation of the two K1 domains.

SEQ ID NO: 15 corresponds to a K1K1 protein of the invention wherein the SEVE linker has been replaced by a GS linker (GSGG) that does not present any structural constrain.

SEQ ID NO: 16 corresponds to a K1K1 protein of the invention wherein the following mutations have been introduced: K10E, R12E, K93E and R95E. K10E and R12E mutations are part of the first kringle domain and K93E and R95E are part of the second kringle domain. The targeted K10, R12, K93 and R95 residues are part of a positively charged patch of the K1 domain interacting with heparin. Since this construct is predicted to have a reduced affinity for heparin, a hexa-histidine tag is added at the C-terminal in order to allow purification by nickel-affinity chromatography.

In particular, the invention relates to a protein comprising or consisting of:
- an amino acid sequence chosen among SEQ ID NO: 9, SEQ ID NO: 13, SEQ ID NO: 14, SEQ ID NO: 15 and SEQ ID NO: 16, or
- an amino acid sequence with at least 80%, preferably 90% identity to a sequence chosen among SEQ ID NO: 9, SEQ ID NO: 13, SEQ ID NO: 14, SEQ ID NO: 15 and SEQ ID NO: 16.

In particular, a protein of the invention comprises or consists of an amino acid sequence having at least 80%, 81%, 82%, 83%, 84%, 85%, 86%, 87%, 88%, 89%, 90%, 91%, 92%, 93%, 94%, 95%, 96%, 97%, 98% or 99% identity to one sequence chosen among SEQ ID NO: 9, SEQ ID NO: 13, SEQ ID NO: 14, SEQ ID NO: 15 and SEQ ID NO: 16.

In particular, the invention relates to a protein comprising or consisting of an amino acid sequence chosen among SEQ ID NO: 9, SEQ ID NO: 13, SEQ ID NO: 14, SEQ ID NO: 15 and SEQ ID NO: 16.

In one embodiment, the invention relates to a protein as defined above, said protein being a synthetic or a recombinant protein.

In the invention, a "synthetic protein" is a protein which is synthesized using classic organic chemistry methods, such as liquid or solid phase synthesis.

In the invention, a "recombinant protein" is a protein resulting from genetic engineering. A genetic construction may be inserted into a vector and expressed in host cells, such as bacteria or yeasts, using classic molecular biology techniques to obtain the recombinant protein.

In one embodiment, the invention relates to a protein as defined above, wherein the activation of the tyrosine kinase receptor MET is heparan sulfate independent.

In in vivo conditions, HGF/SF is immobilized by heparan sulfate chains present in the extracellular matrix, resulting in a severely reduced diffusion and/or tissue distribution.

The protein of the invention is missing the high affinity heparan sulfate binding site (N domain) and therefore is able to diffuse towards MET receptors in distant tissues.

In one embodiment, the invention relates to a protein as defined above, wherein said protein is able to bind the tyrosine kinase receptor MET with a dissociation constant $K_D \leq 200$ nM, preferably ≤100 nM, more preferably ≤10 nM.

In particular, said protein is able to bind the tyrosine kinase receptor MET with a dissociation constant $K_D \leq 200$ nM, ≤150 nM, ≤100 nM, ≤90 nM, ≤80 nM, ≤70 nM, ≤60 nM, ≤50 nM, ≤40 nM, ≤30 nM, ≤10 nM, or ≤5 nM.

In another aspect, the invention also relates to a process to obtain a protein comprising at least two K1 peptide domains, as defined above, comprising the steps of:
- inserting a nucleic acid sequence coding a recombinant protein containing at least two K1 peptide domains, preferably containing two K1 peptide domains, in an expression vector,
- cloning said vector in a host cell, and expressing said recombinant protein,
- extracting and purifying said recombinant protein, said recombinant protein being a protein comprising at least two K1 domains.

In another aspect, the invention relates to a nucleic acid molecule coding a protein of the invention, said nucleic acid preferably consisting of the nucleic acid sequence SEQ ID NO: 10.

TABLE 6

| Nucleic acid coding a C-terminally tagged K1K1 protein. | |
|---|---|
| SEQ ID NO: 10 | ATGGCCATTAGAAACTGCATCATTGGTAAAGGACGCAGCT<br>ACAAGGGAACAGTATCTATCACTAAGAGTGGCATCAAAT<br>GTCAGCCCTGGAGTTCCATGATACCACACGAACACAGCTT<br>TTTGCCTTCGAGCTATCGGGGTAAAGACCTACAGGAAAAC<br>TACTGTCGAAATCCTCGAGGGGAAGAAGGGGGACCCTGG<br>TGTTTCACAAGCAATCCAGAGGTACGCTACGAGGTCTGTG<br>ACATTCCTCAGTGTTCAGAAGTTGAATGCATCATTGGTAA<br>AGGACGCAGCTACAAGGGAACAGTATCTATCACTAAGAG<br>TGGCATCAAATGTCAGCCCTGGAGTTCCATGATACCACAC<br>GAACACAGCTTTTTGCCTTCGAGCTATCGGGGTAAAGACC<br>TACAGGAAAACTACTGTCGAAATCCTCGAGGGGAAGAAG<br>GGGGACCCTGGTGTTTCACAAGCAATCCAGAGGTACGCTA<br>CGAGGTCTGTGACATTCCTCAGTGTAGTGAAGTTGAACAT<br>CATCATCATCATCATTGA |

The nucleic acid sequence SEQ ID NO: 10 encodes the amino acid sequence SEQ ID NO: 9.

In another aspect, the invention relates to an expression vector containing a nucleic acid molecule as defined above, said vector preferably comprising or consisting of the nucleic acid sequence SEQ ID NO: 11.

TABLE 7

Expression vector encoding a K1K1 protein.

SEQ ID NO: 11

GGCCGCACTCGAGTCTGGTAAAGAAACCGCTGCTGCGAAATTTGA
ACGCCAGCACATGGACTCGTCTACTAGCGCAGCTTAATTAACCTA
GGCTGCTGCCACCGCTGAGCAATAACTAGCATAACCCCTTGGGGC
CTCTAAACGGGTCTTGAGGGGTTTTTTGCTGAAAGGAGGAACTAT
ATCCGGATTGGCGAATGGGACGCGCCCTGTAGCGGCGCATTAAGC
GCGGCGGGTGTGGTGGTTACGCGCAGCGTGACCGCTACACTTGCC
AGCGCCCTAGCGCCCGCTCCTTTCGCTTTCTTCCCTTCCTTTCTCGC
CACGTTCGCCGGCTTTCCCCGTCAAGCTCTAAATCGGGGGCTCCC
TTTAGGGTTCCGATTTAGTGCTTTACGGCACCTCGACCCCAAAAA
ACTTGATTAGGGTGATGGTTCACGTAGTGGGCCATCGCCCTGATA
GACGGTTTTTCGCCCTTTGACGTTGGAGTCCACGTTCTTTAATAGT
GGACTCTTGTTCCAAACTGGAACAACACTCAACCCTATCTCGGTC
TATTCTTTTGATTTATAAGGGATTTTGCCGATTTCGGCCTATTGGT
TAAAAAATGAGCTGATTTAACAAAAATTTAACGCGAATTTTAACA
AAATATTAACGTTTACAATTTCTGGCGGCACGATGGCATGAGATT
ATCAAAAAGGATCTTCACCTAGATCCTTTTAAATTAAAAATGAAG
TTTTAAATCAATCTAAAGTATATATGAGTAAACTTGGTCTGACAG
TTACCAATGCTTAATCAGTGAGGCACCTATCTCAGCGATCTGTCT
ATTTCGTTCATCCATAGTTGCCTGACTCCCCGTCGTGTAGATAACT
ACGATACGGGAGGGCTTACCATCTGGCCCCAGTGCTGCAATGATA
CCGCGAGACCCACGCTCACCGGCTCCAGATTTATCAGCAATAAAC
CAGCCAGCCGGAAGGGCCGAGCGCAGAAGTGGTCCTGCAACTTT
ATCCGCCTCCATCCAGTCTATTAATTGTTGCCGGGAAGCTAGAGT
AAGTAGTTCGCCAGTTAATAGTTTGCGCAACGTTGTTGCCATTGCT
ACAGGCATCGTGGTGTCACGCTCGTCGTTTGGTATGGCTTCATTCA
GCTCCGGTTCCCAACGATCAAGGCGAGTTACATGATCCCCCATGT
TGTGCAAAAAAGCGGTTAGCTCCTTCGGTCCTCCGATCGTTGTCA
GAAGTAAGTTGGCCGCAGTGTTATCACTCATGGTTATGGCAGCAC
TGCATAATTCTCTTACTGTCATGCCATCCGTAAGATGCTTTTCTGT
GACTGGTGAGTACTCAACCAAGTCATTCTGAGAATAGTGTATGCG
GCGACCGAGTTGCTCTTGCCCGGCGTCAATACGGGATAATACCGC
GCCACATAGCAGAACTTTAAAAGTGCTCATCATTGGAAAACGTTC
TTCGGGGCGAAAACTCTCAAGGATCTTACCGCTGTTGAGATCCAG
TTCGATGTAACCCACTCGTGCACCCAACTGATCTTCAGCATCTTTT
ACTTTCACCAGCGTTTCTGGGTGAGCAAAAACAGGAAGGCAAAA
TGCCGCAAAAAAGGGAATAAGGGCGACACGGAAATGTTGAATAC
TCATACTCTTCCTTTTTCAATCATGATTGAAGCATTTATCAGGGTT
ATTGTCTCATGAGCGGATACATATTTGAATGTATTTAGAAAAATA
AACAAATAGGTCATGACCAAAATCCCTTAACGTGAGTTTTCGTTC
CACTGAGCGTCAGACCCCGTAGAAAAGATCAAAGGATCTTCTTGA
GATCCTTTTTTTCTGCGCGTAATCTGCTGCTTGCAAACAAAAAAAC
CACCGCTACCAGCGGTGGTTTGTTTGCCGGATCAAGAGCTACCAA
CTCTTTTTCCGAAGGTAACTGGCTTCAGCAGAGCGCAGATACCAA
ATACTGTCCTTCTAGTGTAGCCGTAGTTAGGCCACCACTTCAAGA
ACTCTGTAGCACCGCCTACATACCTCGCTCTGCTAATCCTGTTACC
AGTGGCTGCTGCCAGTGGCGATAAGTCGTGTCTTACCGGGTTGGA
CTCAAGACGATAGTTACCGGATAAGGCGCAGCGGTCGGGCTGAA
CGGGGGGTTCGTGCACACAGCCCAGCTTGGAGCGAACGACCTAC
ACCGAACTGAGATACCTACAGCGTGAGCTATGAGAAAGCGCCAC
GCTTCCCGAAGGGAGAAAGGCGGACAGGTATCCGGTAAGCGGCA
GGGTCGGAACAGGAGAGCGCACGAGGGAGCTTCCAGGGGGAAAC
GCCTGGTATCTTTATAGTCCTGTCGGGTTTCGCCACCTCTGACTTG
AGCGTCGATTTTTGTGATGCTCGTCAGGGGGCGGAGCCTATGGA
AAAACGCCAGCAACGCGGCCTTTTTACGGTTCCTGGCCTTTTGCT
GGCCTTTTGCTCACATGTTCTTTCCTGCGTTATCCCCTGATTCTGTG
GATAACCGTATTACCGCCTTTGAGTGAGCTGATACCGCTCGCCGC
AGCCGAACGACCGAGCGCAGCGAGTCAGTGAGCGAGGAAGCGGA
AGAGCGCCTGATGCGGTATTTTCTCCTTACGCATCTGTGCGGTATT
TCACACCGCATATATGGTGCACTCTCAGTACAATCTGCTCTGATG
CCGCATAGTTAAGCCAGTATACACTCCGCTATCGCTACGTGACTG
GGTCATGGCTGCGCCCCGACACCCGCCAACACCCGCTGACGCGCC
CTGACGGGCTTGTCTGCTCCCGGCATCCGCTTACAGACAAGCTGT
GACCGTCTCCGGGAGCTGCATGTGTCAGAGGTTTTCACCGTCATC
ACCGAAACGCGCGAGGCAGCTGCGGTAAAGCTCATCAGCGTGGT
CGTGAAGCGATTCACAGATGTCTGCCTGTTCATCCGCGTCCAGCT
CGTTGAGTTTCTCCAGAAGCGTTAATGTCTGGCTTCTGATAAAGC
GGGCCATGTTAAGGGCGGTTTTTTCCTGTTTGGTCACTGATGCCTC
CGTGTAAGGGGGATTTCTGTTCATGGGGGTAATGATACCGATGAA
ACGAGAGAGGATGCTCACGATACGGGTTACTGATGATGAACATG
CCCGGTTACTGGAACGTTGTGAGGGTAAACAACTGGCGGTATGGA
TGCGGCGGGACCAGAGAAAAATCACTCAGGGTCAATGCCAGCGC
TTCGTTAATACAGATGTAGGTGTTCCACAGGGTAGCCAGCAGCAT
CCTGCGATGCAGATCCGGAACATAATGGTGCAGGGCGCTGACTTC
CGCGTTTCCAGACTTTACGAAACACGGAAACCGAAGACCATTCAT
GTTGTTGCTCAGGTCGCAGACGTTTTGCAGCAGCAGTCGCTTCAC
GTTCGCTCGCGTATCGGTGATTCATTCTGCTAACCAGTAAGGCAA
CCCCGCCAGCCTAGCCGGGTCCTCAACGACAGGAGCACGATCATG
CTAGTCATGCCCCGCGCCCACCGGAAGGAGCTGACTGGGTTGAAG

TABLE 7-continued

Expression vector encoding a K1K1 protein.

```
GCTCTCAAGGGCATCGGTCGAGATCCCGGTGCCTAATGAGTGAGC
TAACTTACATTAATTGCGTTGCGCTCACTGCCCGCTTTCCAGTCGG
GAAACCTGTCGTGCCAGCTGCATTAATGAATCGGCCAACGCGCGG
GGAGAGGCGGTTTGCGTATTGGGCGCCAGGGTGGTTTTTCTTTTC
ACCAGTGAGACGGGCAACAGCTGATTGCCCTTCACCGCCTGGCCC
TGAGAGAGTTGCAGCAAGCGGTCCACGCTGGTTTGCCCCAGCAGG
CGAAAATCCTGTTTGATGGTGGTTAACGGCGGGATATAACATGAG
CTGTCTTCGGTATCGTCGTATCCCACTACCGAGATGTCCGCACCA
ACGCGCAGCCCGGACTCGGTAATGGCGCGCATTGCGCCCAGCGCC
ATCTGATCGTTGGCAACCAGCATCGCAGTGGGAACGATGCCCTCA
TTCAGCATTTGCATGGTTTGTTGAAAACCGGACATGGCACTCCAG
TCGCCTTCCCGTTCCGCTATCGGCTGAATTTGATTGCGAGTGAGAT
ATTTATGCCAGCCAGCCAGACGCAGACGCGCCGAGACAGAACTT
AATGGGCCCGCTAACAGCGCGATTTGCTGGTGACCCAATGCGACC
AGATGCTCCACGCCCAGTCGCGTACCGTCTTCATGGGAGAAAATA
ATACTGTTGATGGGTGTCTGGTCAGAGACATCAAGAAATAACGCC
GGAACATTAGTGCAGGCAGCTTCCACAGCAATGGCATCCTGGTCA
TCCAGCGGATAGTTAATGATCAGCCCACTGACGCGTTGCGCGAGA
AGATTGTGCACCGCCGCTTTACAGGCTTCGACGCCGCTTCGTTCTA
CCATCGACACCACCACGCTGGCACCCAGTTGATCGGCGCGAGATT
TAATCGCCGCGACAATTTGCGACGGCGCGTGCAGGGCCAGACTG
GAGGTGGCAACGCCAATCAGCAACGACTGTTTGCCCGCCAGTTGT
TGTGCCACGCGGTTGGGAATGTAATTCAGCTCCGCCATCGCCGCT
TCCACTTTTTCCCGCGTTTTCGCAGAAACGTGGCTGGCCTGGTTCA
CCACGCGGGAAACGGTCTGATAAGAGACACCGGCATACTCTGCG
ACATCGTATAACGTTACTGGTTTCACATTCACCACCCTGAATTGAC
TCTCTTCCGGGCGCTATCATGCCATACCGCGAAAGGTTTTGCGCC
ATTCGATGGTGTCCGGGATCTCGACGCTCTCCCTTATGCGACTCCT
GCATTAGGAAGCAGCCCAGTAGTAGGTTGAGGCCGTTGAGCACC
GCCGCCGCAAGGAATGGTGCATGCAAGGAGATGGCGCCCAACAG
TCCCCCGGCCACGGGGCCTGCCACCATACCCACGCCGAAACAAGC
GCTCATGAGCCCGAAGTGGCGAGCCCGATCTTCCCCATCGGTGAT
GTCGGCGATATAGGCGCCAGCAACCGCACCTGTGGCGCCGGTGAT
GCCGGCCACGATGCGTCCGGCGTAGAGGATCGAGATCGATCTCG
ATCCCGCGAAATTAATACGACTCACTATAGGGGAATTGTGAGCGG
ATAACAATTCCCCTCTAGAAATAATTTTGTTTAACTTTAAGAAGG
AGATATACCATGGCCATTAGAAACTGCATCATTGGTAAAGGACGC
AGCTACAAGGGAACAGTATCTATCACTAAGAGTGGCATCAAATGT
CAGCCCTGGAGTTCCATGATACCACACGAACACAGCTTTTTGCCT
TCGAGCTATCGGGTAAAGACCTACAGGAAAACTACTGTCGAAA
TCCTCGAGGGGAAGAAGGGGGACCCTGGTGTTTCACAAGCAATC
CAGAGGTACGCTACGAGGTCTGTGACATTCCTCAGTGTTCAGAAG
TTGAATGCATCATTGGTAAAGGACGCAGCTACAAGGGAACAGTA
TCTATCACTAAGAGTGGCATCAAATGTCAGCCCTGGAGTTCCATG
ATACCACACGAACACAGCTTTTTGCCTTCGAGCTATCGGGGTAAA
GACCTACAGGAAAACTACTGTCGAAATCCTCGAGGGGAAGAAGG
GGGACCCTGGTGTTTCACAAGCAATCCAGAGGTACGCTACGAGGT
CTGTGACATTCCTCAGTGTAGTGAAGTTGAACATCATCATCATCA
TCATTGATGAGC
```

In another aspect, the invention relates to a host cell containing an expression vector as defined above, said host cell being preferably chosen among the group consisting of yeast cells and bacterial cells.

In another aspect, the invention also relates to a composition comprising:
- a protein as defined above, or
- a nucleic acid molecule coding said protein, or
- an expression vector containing said nucleic acid molecule, or
- a host cell containing said expression vector.

In another aspect, the invention also relates to a protein as defined above, for use in an in vivo diagnostic method.

Due to its capacity to bind MET the protein of the invention represents a valuable tool for diagnostic methods, in particular for pathologies which implicate expression of HGF/SF and MET molecules.

In an embodiment, the invention relates to a protein as defined above, for use in a diagnostic method of a pathology chosen among: cancers, diseases of epithelial organs including acute and chronic liver diseases, acute and chronic kidney diseases, chronic lung diseases and chronic skin wounds, diseases of the central nervous system including neuron diseases and sclerosis, ischemic heart diseases, peripheral vascular diseases, diabetes and associated complications such as peripheral neuropathies.

In an embodiment, the invention relates to a protein as defined above, for use in a in vivo diagnostic method of a pathology chosen among: cancers, diseases of epithelial organs including acute and chronic liver diseases, acute and chronic kidney diseases, chronic lung diseases and chronic skin wounds, diseases of the central nervous system including neuron diseases and sclerosis, ischemic heart diseases, peripheral vascular diseases, diabetes and associated complications such as peripheral neuropathies.

In an embodiment, the invention relates to a protein as defined above, for use in an in vivo diagnostic method, wherein said cancers are tumors expressing the tyrosine kinase receptor MET.

In another aspect, the invention relates to a protein as defined above, for use in medical imaging.

In another aspect, the invention relates to a protein as defined above, for use in in vivo imaging.

In an embodiment, the invention relates to a protein as defined above, for use in medical imaging, wherein said protein allows the detection and/or the tracking of drugs and/or imaging agent.

In particular, the protein of the invention can be used in image guided surgery. Pre- and intra-operative imaging is currently used to assist surgeons in the careful positioning of surgical tools as well as guiding the complete removal of specific tissue. Fluorescent (IR/NIR) probes may be used for live imaging during operation.

In another aspect, the invention relates to the use of a protein as defined above, as an in vitro diagnostic tool.

In an embodiment, the invention relates to the use of a protein as defined above for the in vitro diagnostic of a pathology, said pathology being chosen among: cancers, diseases of epithelial organs including acute and chronic liver diseases, acute and chronic kidney diseases, chronic lung diseases and chronic skin wounds, diseases of the central nervous system including neuron diseases and sclerosis, ischemic heart diseases, peripheral vascular diseases, diabetes and associated complications such as peripheral neuropathies.

In an embodiment, the invention relates to the use of the protein for the in vitro diagnostic of a pathology as defined above, wherein said cancers are tumors expressing the tyrosine kinase receptor MET.

In another aspect, the invention relates to the use of a protein of the invention for the in vitro or ex vivo imaging.

In diagnostic methods and medical imagery, the protein can be detected and quantified in biological samples by dosage (for example using a biopsy) or by pictures (obtained from technologies such as PET scan or IRM).

Indeed, the protein of the invention can be labelled with a marker and allows the detection, localization and quantification of MET receptors.

For example, the protein can be labelled with radiopharmaceutical tracers or fluorescent tracers.

Such radiopharmaceutical tracers include, but are not limited to, Calcium-47, Carbon-11, Carbon-14, Chromium-51, Cobalt-57, Cobalt-58, Erbium-169, Fluorine-18, Gallium-67, Gallium-68, Hydrogen-3, Indium-111, Iodine-123, Iodine-125, Iodine-131, Iron-59, Krypton-81m, Nitrogen-13, Oxygen-15, Phosphorus-32, Radium-223, Rubidium-82, Samarium-153, Selenium-75, Sodium-22, Sodium-24, Strontium-89, Technetium-99m, Thallium-201, Xenon-133 and Yttrium-90.

Such fluorescent tracers include, but are not limited to, fluorescent dyes (such as rhodamine derivatives, coumarin derivatives, fluorescein derivatives, . . . ) or fluorescent proteins (such as GFP (green), YFP (yellow), RFP (red), or phytochrome-based near-infrared fluorescent protein (iRFP).

In particular, infrared (IR) and near infrared (NIR) dyes and fluorescent proteins are preferred tracers for in vivo imaging due to increased penetration and reduced autofluorescence.

In another aspect, the invention relates to a method for the in vivo diagnosis of a pathology, comprising a step of administering a protein as defined above, to a patient, said pathology being chosen among: cancers, diseases of epithelial organs including acute and chronic liver diseases, acute and chronic kidney diseases, chronic lung diseases and chronic skin wounds, diseases of the central nervous system including neuron diseases and sclerosis, ischemic heart diseases, peripheral vascular diseases, diabetes and associated complications such as peripheral neuropathies.

In another aspect, the invention relates to a method for medical imaging comprising a step of administering a protein as defined above to a patient.

In an embodiment, the invention relates to a method for medical imaging, wherein said protein allows the detection of the tyrosine kinase receptor MET.

In an embodiment, the invention relates to a method for medical imaging, wherein said protein allows the pretargeting of an antibody.

Indeed, the protein of the invention can be linked to an antibody that recognizes a specific epitope of a tracer.

In another aspect, the invention also relates to a pharmaceutical composition comprising:
  a protein as defined above or
  a nucleic acid molecule coding said protein, or
  an expression vector containing said nucleic acid molecule, or
  a host cell containing said expression vector, and
a pharmaceutically acceptable vehicle.

In another aspect, the invention also relates to a protein as defined above, for use as a medicament.

In an embodiment, the invention relates to a protein as defined above, for use in the treatment of tissue injuries by promoting cell survival or tissue regeneration.

In an embodiment, the invention relates to a protein as defined above, for use in the treatment of a pathology chosen among: diseases of epithelial organs including acute and chronic liver diseases, acute and chronic kidney diseases, chronic lung diseases and chronic skin wounds, diseases of the central nervous system including neuron diseases and sclerosis, ischemic heart diseases, peripheral vascular diseases, diabetes and associated complications such as peripheral neuropathies.

In an embodiment, the invention relates to a protein as defined above, for use in the treatment of tissue injuries or for use in the treatment of a pathology as defined above, said protein being administrable at a dose comprised from about 1 mg/kg to 1,000 mg/kg, preferably from about 10 mg/kg to about 100 mg/kg.

In an embodiment, the invention relates to a protein as defined above, for use in the treatment of tissue injuries or for use in the treatment of a pathology as defined above, said protein being used under a form liable to be administrable by oral or intravenous route at an unitary dose comprised from 1 mg to 1,000 mg, in particular from 10 mg to 1,000 mg, in particular from 100 to 1,000 mg.

In another aspect, the invention also relates to the use of the protein as defined above to promote angiogenesis, in in vivo, ex vivo or in vitro conditions.

Due to its potent MET agonistic activity, the protein of the invention can be used to understand the mechanism of interaction between MET and HGF/SF.

In another aspect, the invention relates to the use of a protein as defined above, as an in vitro research tool.

In another aspect, the invention also relates to a molecular complex between a protein as defined above and a tyrosine kinase receptor MET, said protein being complexed with said tyrosine kinase receptor MET by at least two K1 domains.

The invention will be better explained by the following figures and examples. In any case, the following examples should not be considered as restricting the scope of the invention.

LEGENDS TO THE FIGURES

FIG. 1. Plasmid used for expression of K1K1 in *E. coli*. The two copies of the K1 domain (aa 128-206) of HGF/SF are arranged in head-to-tail orientation (in tandem) and expressed under the control of the lac promoter.

Figure 2:
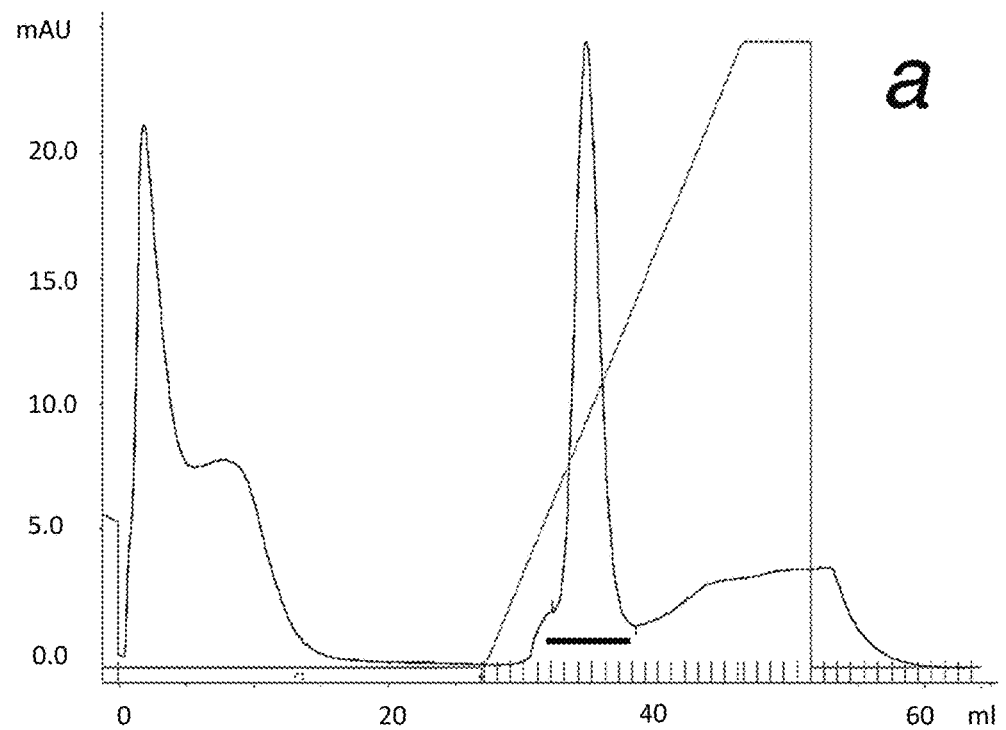
Figure 2:
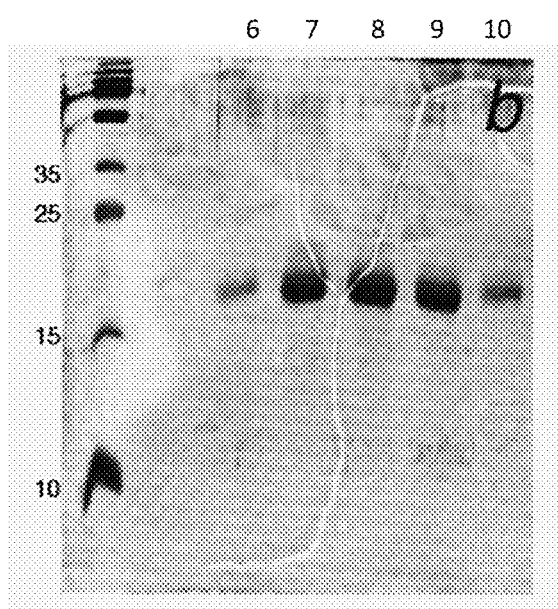

FIG. 2. HisTrap purification of the K1K1 protein from inclusion bodies of *E. coli* BL21 culture. (a) Elution profile. The fractions corresponding to the main protein peak bound the HisTrap (black bar) (6, 7, 8, 9 and 10) were analyzed by SDS-PAGE under reducing conditions and are shown in (b).

Figure 3:
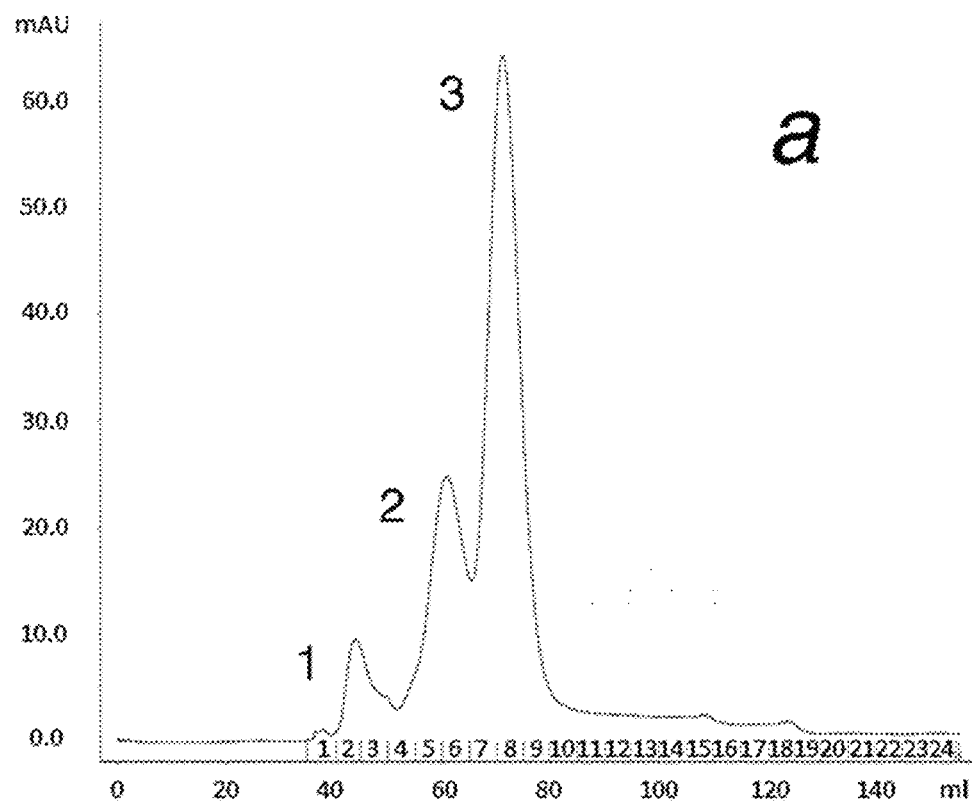
Figure 3:
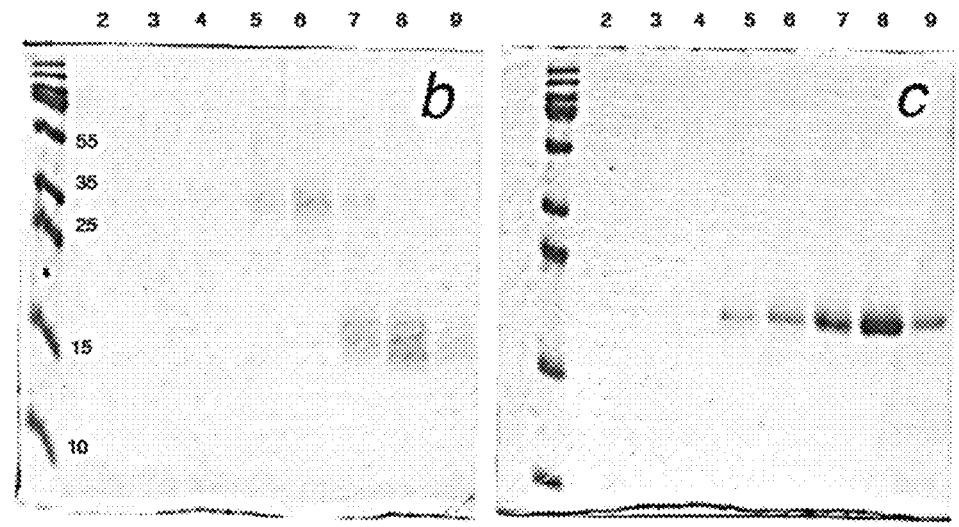

FIG. 3. Size exclusion chromatography of the K1K1 protein. The fractions corresponding to the main peak from the His-Trap column (FIG. 2) were pooled, concentrated and an aliquot was loaded on a Superdex column (a). Fractions across the three peaks were analyzed by SDS-PAGE under non-reducing (b) or reducing conditions (c). Both peaks 2 and 3 contain predominantly the K1K1 protein (peak 2 contains a dimer of dimer whereas peak 3 contains the expected dimer). Non-reducing gel shows the prewash His-Trap purification of the K1K1 protein from inclusion bodies.

Figure 4:
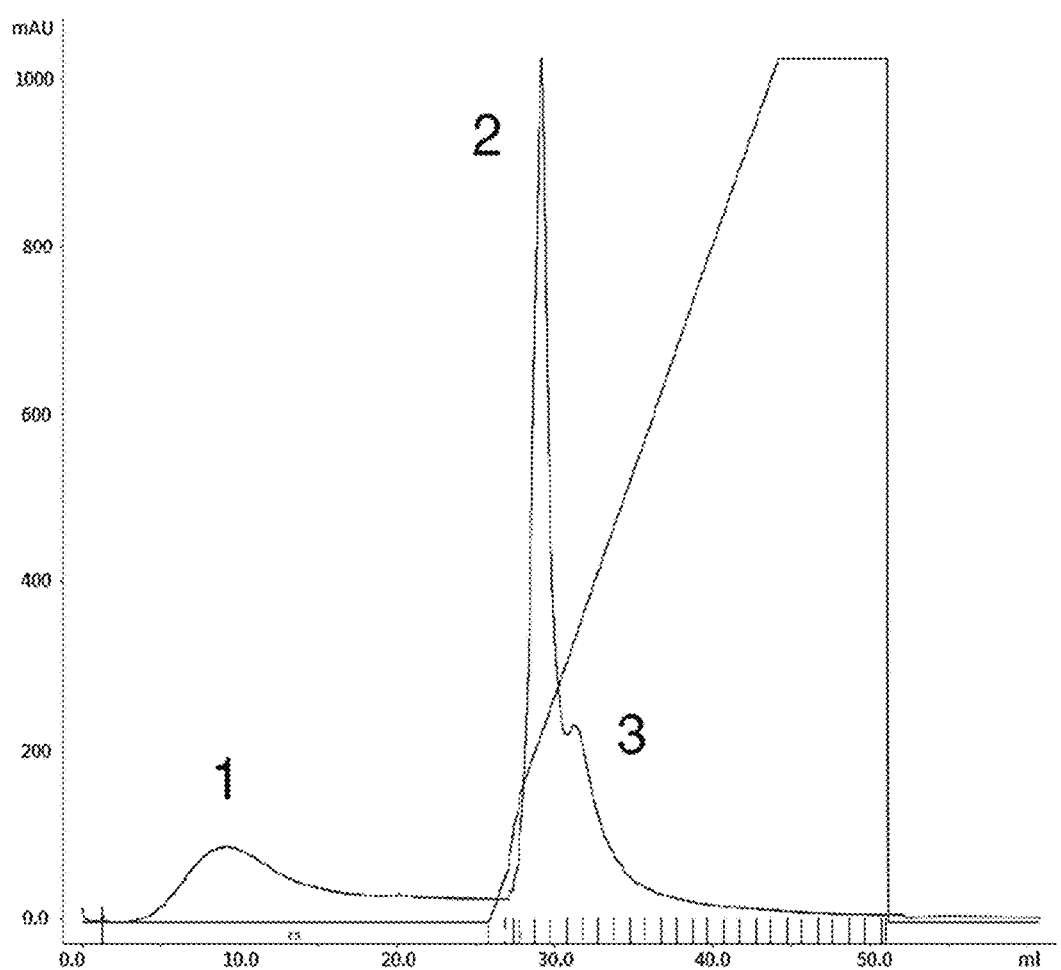

FIG. 4. Cation exchange chromatography of the K1K1 protein. The fractions corresponding to the main peak from the His-Trap column (FIG. 2) were pooled, concentrated and an aliquot was loaded on a 1 ml Resource-S column (a). The unbound material (peak 1) as well as fractions eluted with a NaCl gradient were tested for biological activity in the MDCK colony scatter assay. All activity was recovered in peak 2.

Figure 5:
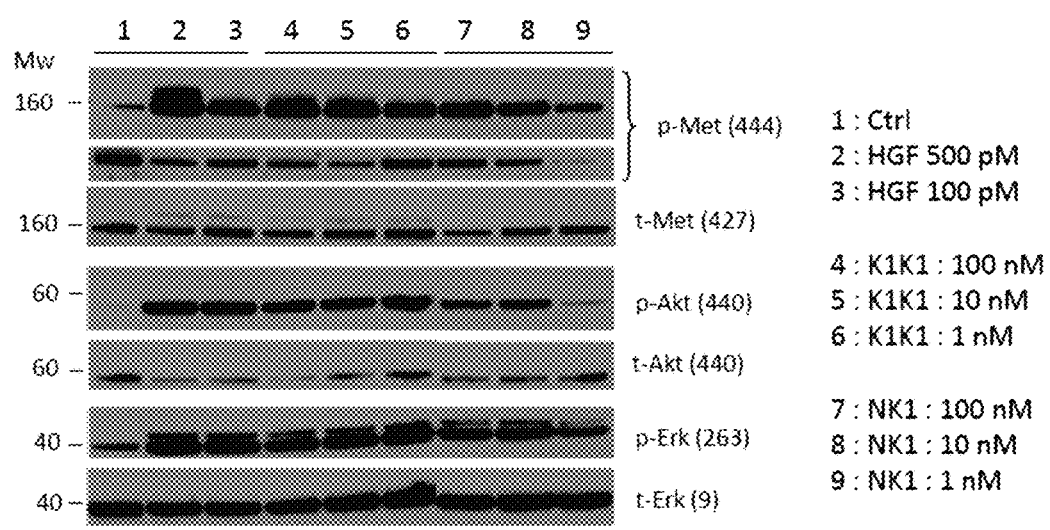

FIG. 5. MET signaling analysis upon K1K1 stimulation. HeLa cells were treated with 100 and 500 pM HGF/SF (HGF), 1, 10, and 100 nM K1K1 and 1, 10, and 100 nM NK1. Cell lysates were then analyzed by specific total MET, Akt and ERK or phospho-MET, phospho-Akt and phospho-ERK western blot. Ctrl: DMEM 0.1% FCS (Fetal Calf Serum).

Figure 6:
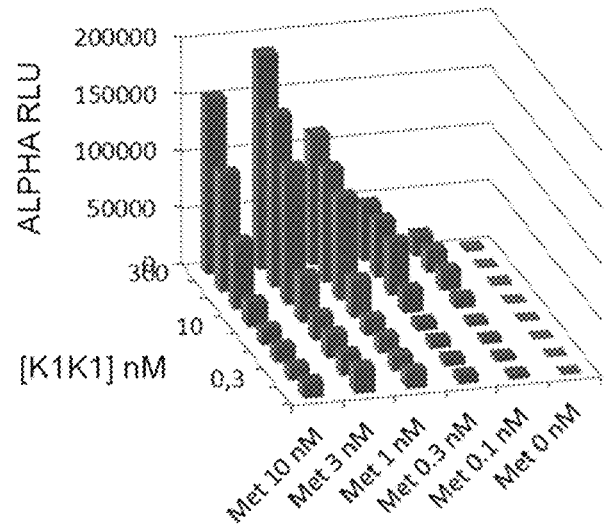
Figure 6:
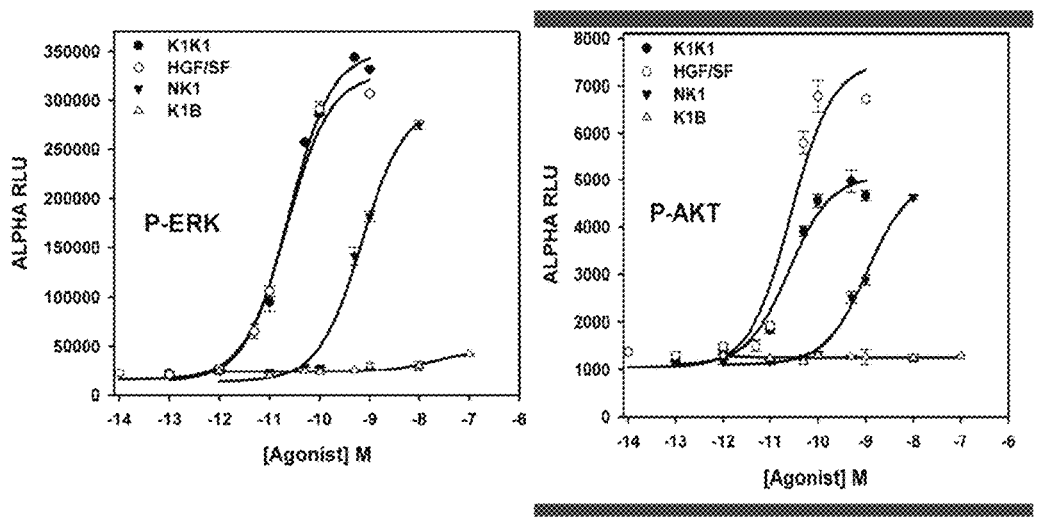

FIG. 6. ALPHAscreen® MET-Fc-K1K1 and ERK/Akt activation. (a) Alphascreen MET-Fc-K1K1. Cross-titration assays for binding of K1K1 to recombinant MET-Fc protein were performed in 384-well microtiter plates. Final concentrations were 0-300 nM for K1K1, 0-10 nM for MET-Fc, 10 µg/mL for streptavidin coated donor beads and protein A-conjugated acceptor beads. (b) Akt and ERK phosphorylation by quantitative ALPHA Assay. Cells were plated, stimulated with different agonists (HGF/SF, NK1, K1K1 and K1B (biotinylated K1)), and then lysed in the same 96-well culture plate. ALPHAScreen® SureFire® Ultra™ acceptor and donor beads were added and incubated for 2 hours. The emitted signal intensity was measured using standard Alpha settings on an EnSpire® Multimode Plate Reader (PerkinElmer).

Figure 7:
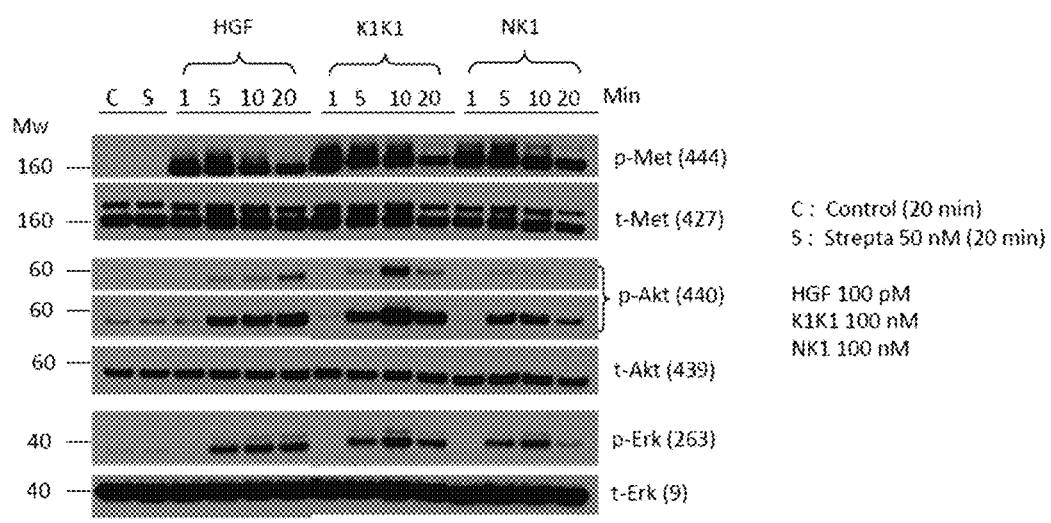

FIG. 7. MET signaling analysis upon K1K1 stimulation. HeLa cells were treated with 100 pM HGF/SF, 100 nM K1K1 or 100 nM NK1, for 1, 5, 10 or 20 min. Cell lysates were then analyzed by specific total MET, Akt and ERK or phospho-MET, phospho-Akt and phospho-ERK western blot.

Figure 8:
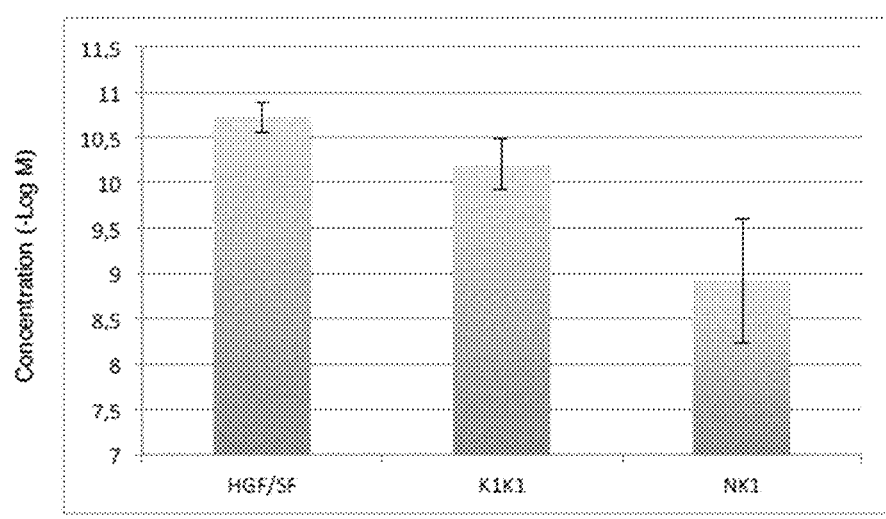

FIG. 8. Biological activity of the K1K1 protein. The MDCK colony scattering activity of the K1K1 protein (HisTrap pool) was tested and compared to those of purified, recombinant full-length HGF/SF and NK1. Data are mean±standard deviations from 5 (HGF/SF), 7 (K1K1) and 7 (NK1) experiments respectively.

Figure 9:
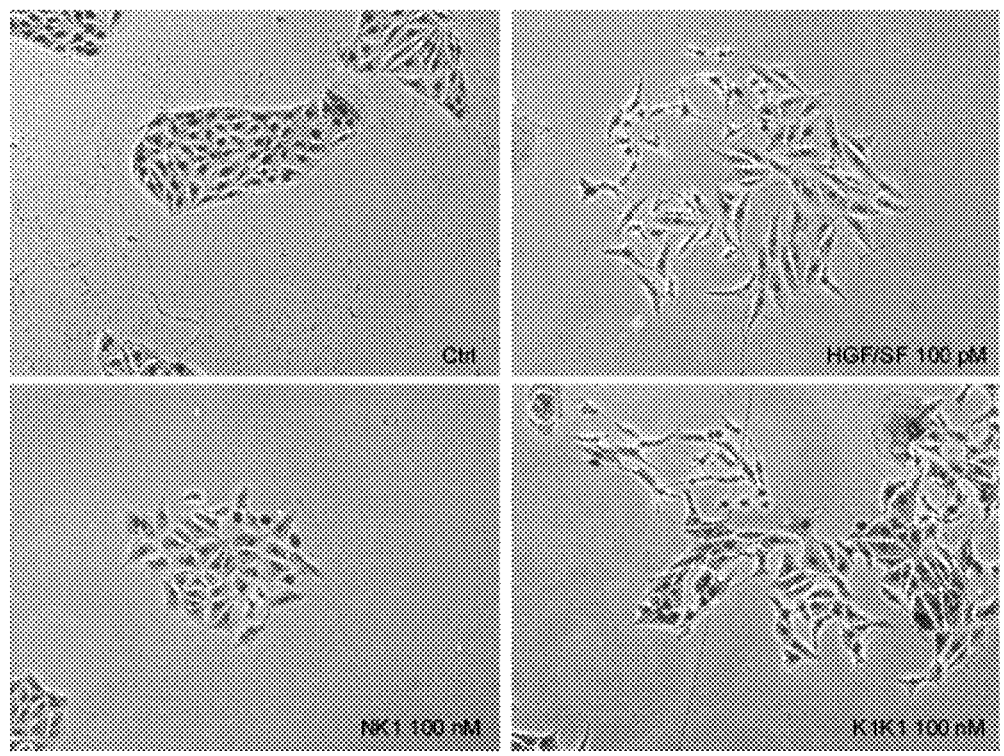
Figure 10A:
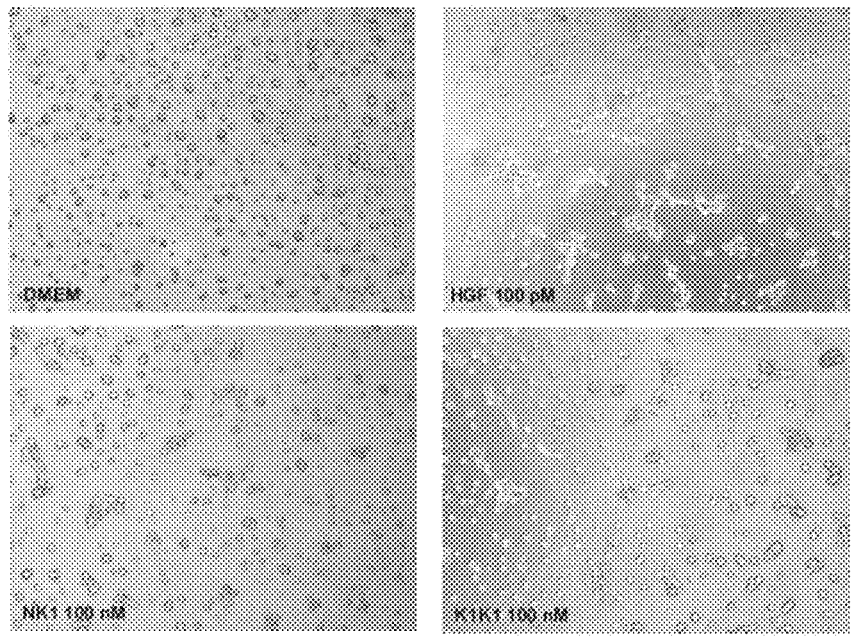
Figure 10A:
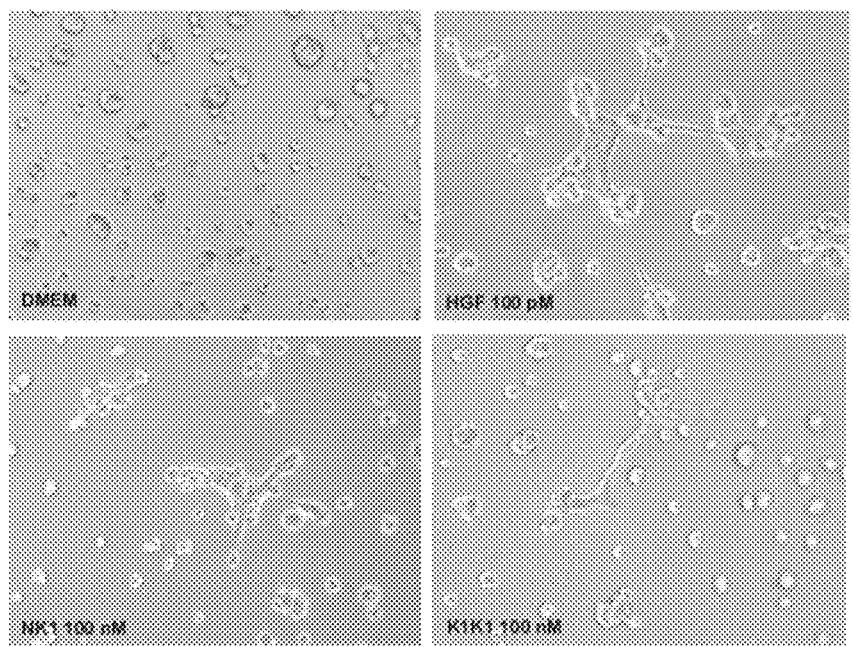
Figure 10B:
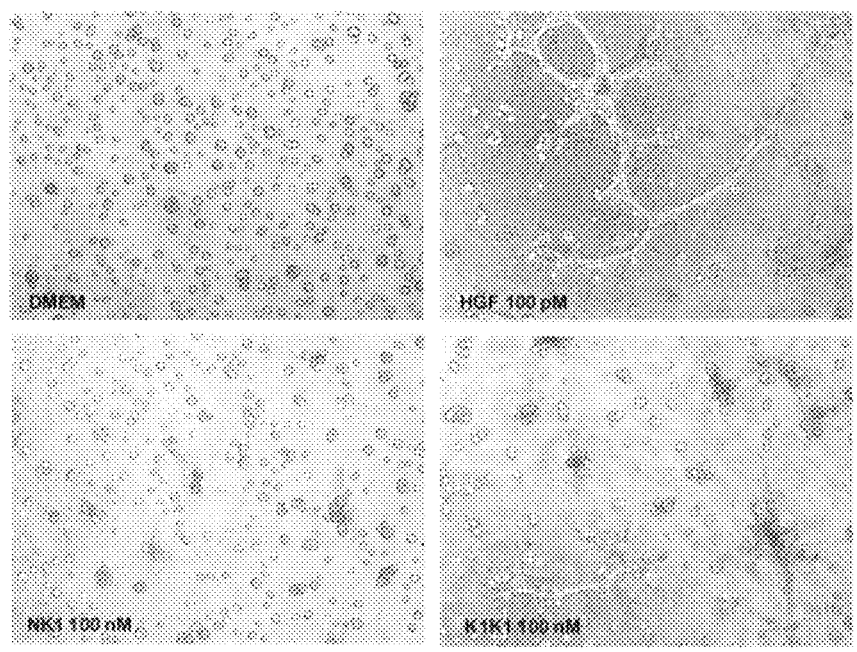
Figure 10B:
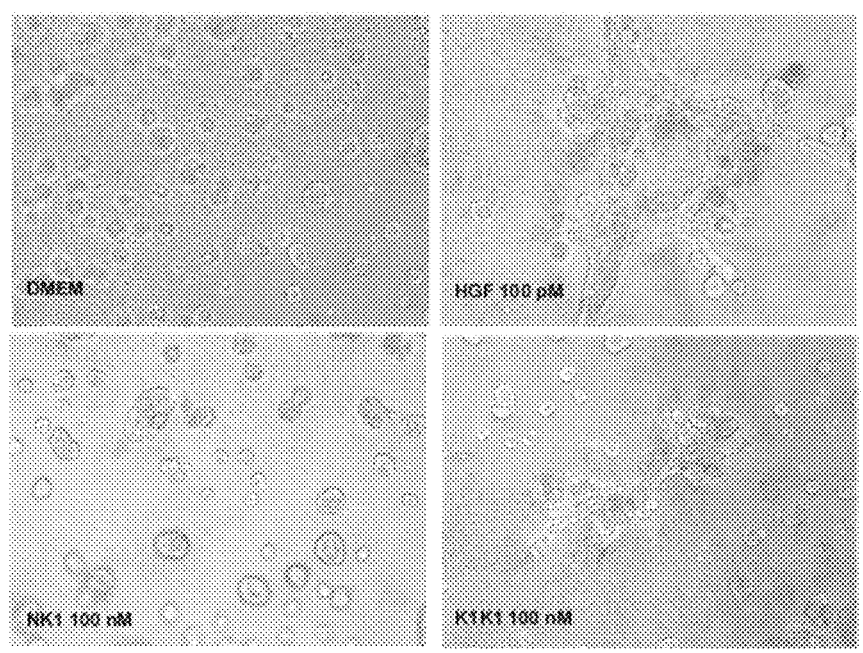

FIG. 9. Cellular phenotypes induced by K1K1 protein (Cell scattering assay). MDCK isolated cell islets were incubated in culture media with 100 pM HGF/SF, 100 nM NK1, 100 nM K1K1. Cells were then stained and observed under a microscope (at 100× magnification).

FIG. 10. Cellular phenotypes induced by K1K1 protein (Matrigel™ morphogenesis assay). MDCK cells were seeded onto a layer of Matrigel™ and treated with 100 pM HGF/SF, 100 nM NK1 and 100 nM K1K1. Cells were then observed under a microscope at 40× or 100× magnification, after one day of culture (a) and after two days of culture (b).

Figure 11:
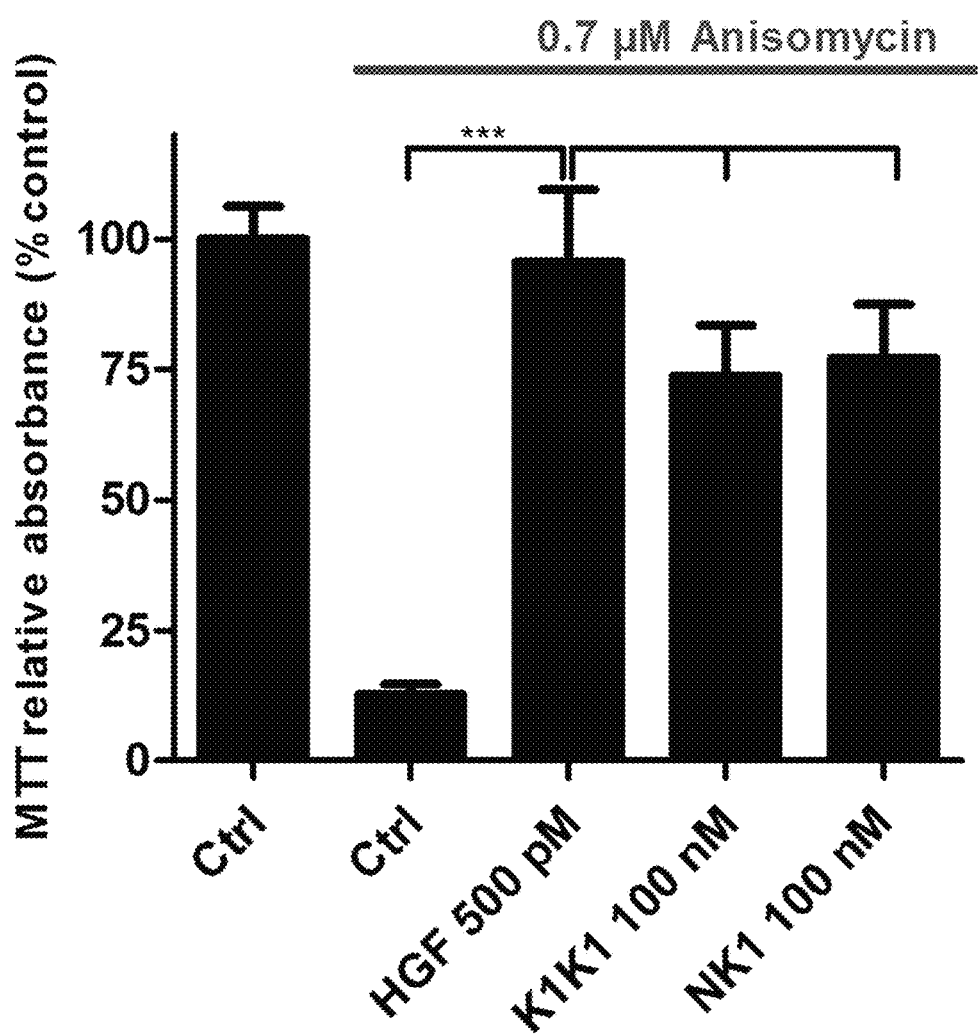

FIG. 11. Cellular phenotypes (MTT Assay). MDCK cells were cultured overnight (15 h) in medium with or without anisomycin (0.7 µM) and in the presence of 500 pM HGF/SF (HGF), 100 nM K1K1, and 100 nM NK1. An MTT assay was then performed to evaluate cell survival. Results are expressed as the percentage of untreated control. An ANOVA test was performed to compare the 3 means, with a P-value<0.05 considered statistically significant. ANOVA tests were performed to compare all the means, and a P-value<0.001 was considered to indicate a statistically significant difference.

Figure 12:
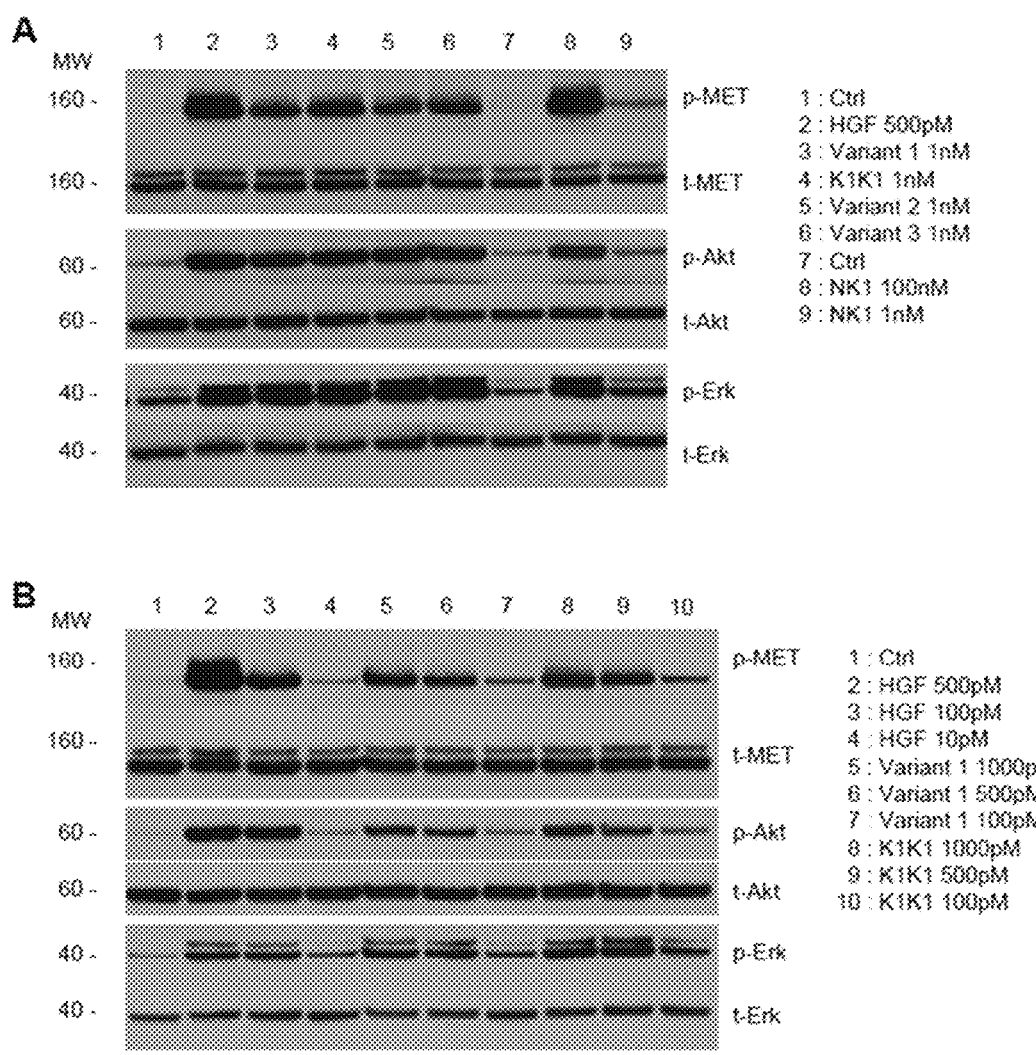

FIG. 12. MET signaling analysis upon K1K1 stimulation. (A) HeLa cells were treated with 500 pM HGF/SF (HGF), 1 nM K1K1, 1 nM variant 1, 1 nM variant 2, 1 nM variant 3, and 1 and 100 nM NK1. (B) HeLa cells were treated with 10, 100 and 500 pM HGF/SF (HGF), 100, 500, and 1000 pM Variant 1, and 100, 500 and 1000 pM K1K1. Cell lysates were then analyzed by specific total MET, Akt and ERK or phospho-MET, phospho-Akt and phospho-ERK western blot. Ctrl: K1 monomer.

Figure 13:
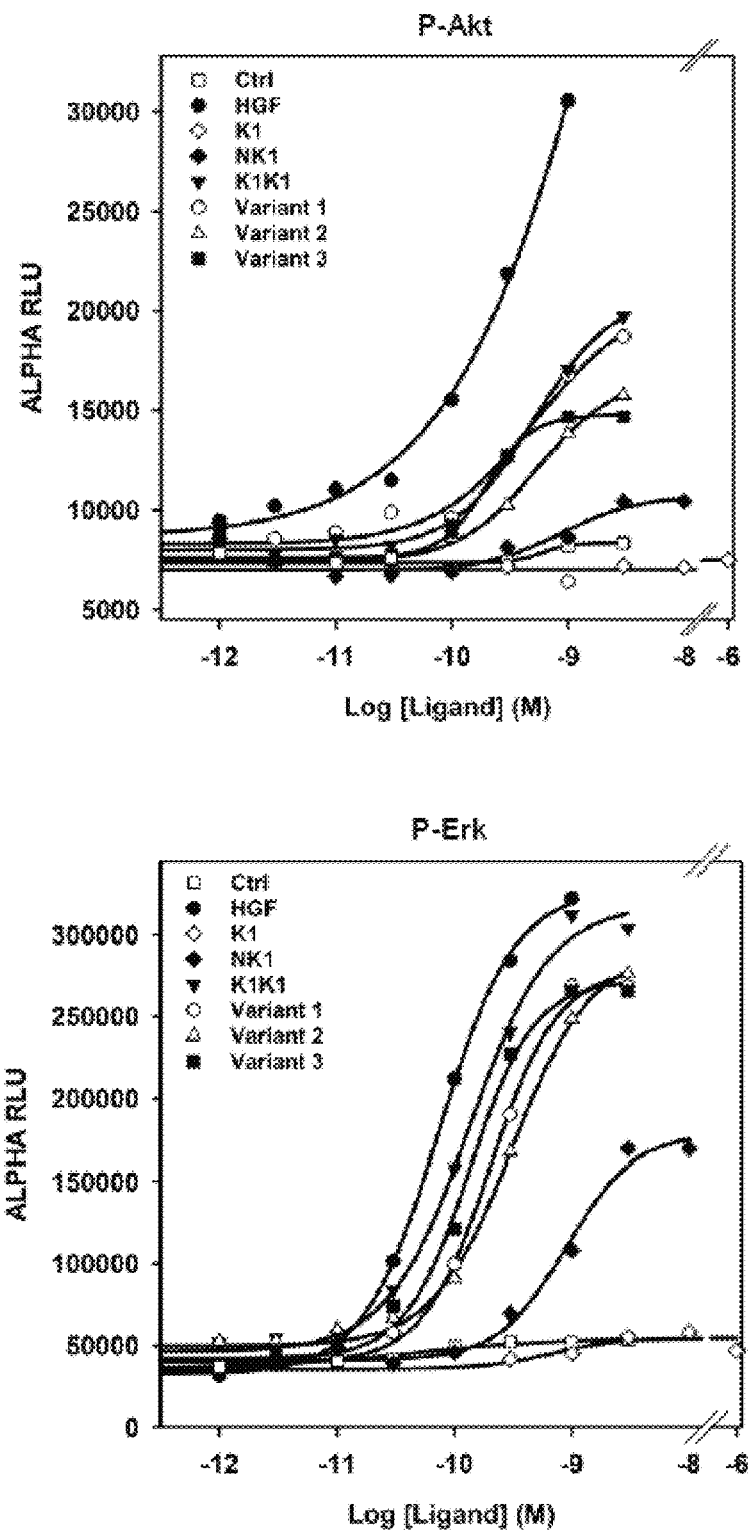

FIG. 13. Akt and ERK Phosphorylation by quantitative ALPHA Assay. Cells were plated, stimulated with increasing concentrations of various agonists (HGF/SF, NK1, K1K1 and variants 1, 2 and 3) for 10 min, and then lysed in the same 96-well culture plate. ALPHAScreen® SureFire® reaction mixtures were added and incubated for 2 hours according to manufacturer protocol (TGRES500 and TGRA4S500). The emitted signal intensity was measured using standard Alpha settings on an EnSpire® Multimode Plate Reader (PerkinElmer).

Figure 14:
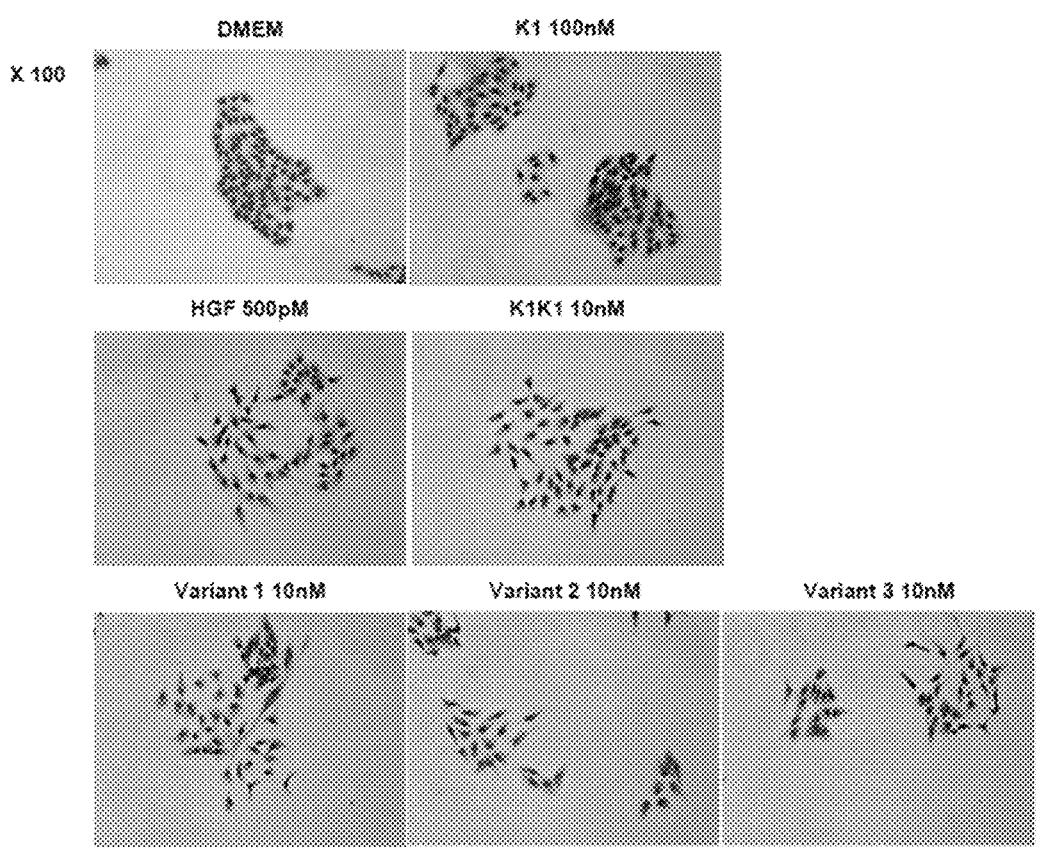

FIG. 14. Cellular phenotypes induced by K1K1 protein (Cell scattering assay). MDCK isolated cell islets were incubated in culture media with 500 pM HGF/SF, 1, 10, and 100 nM K1K1, 10 nM K1K1 variant 1, 2, and 3, and 100 nM K1 monomer. Cells were then stained and observed under microscope (100×). Ctrl: DMEM 10% FCS.

Figure 15:
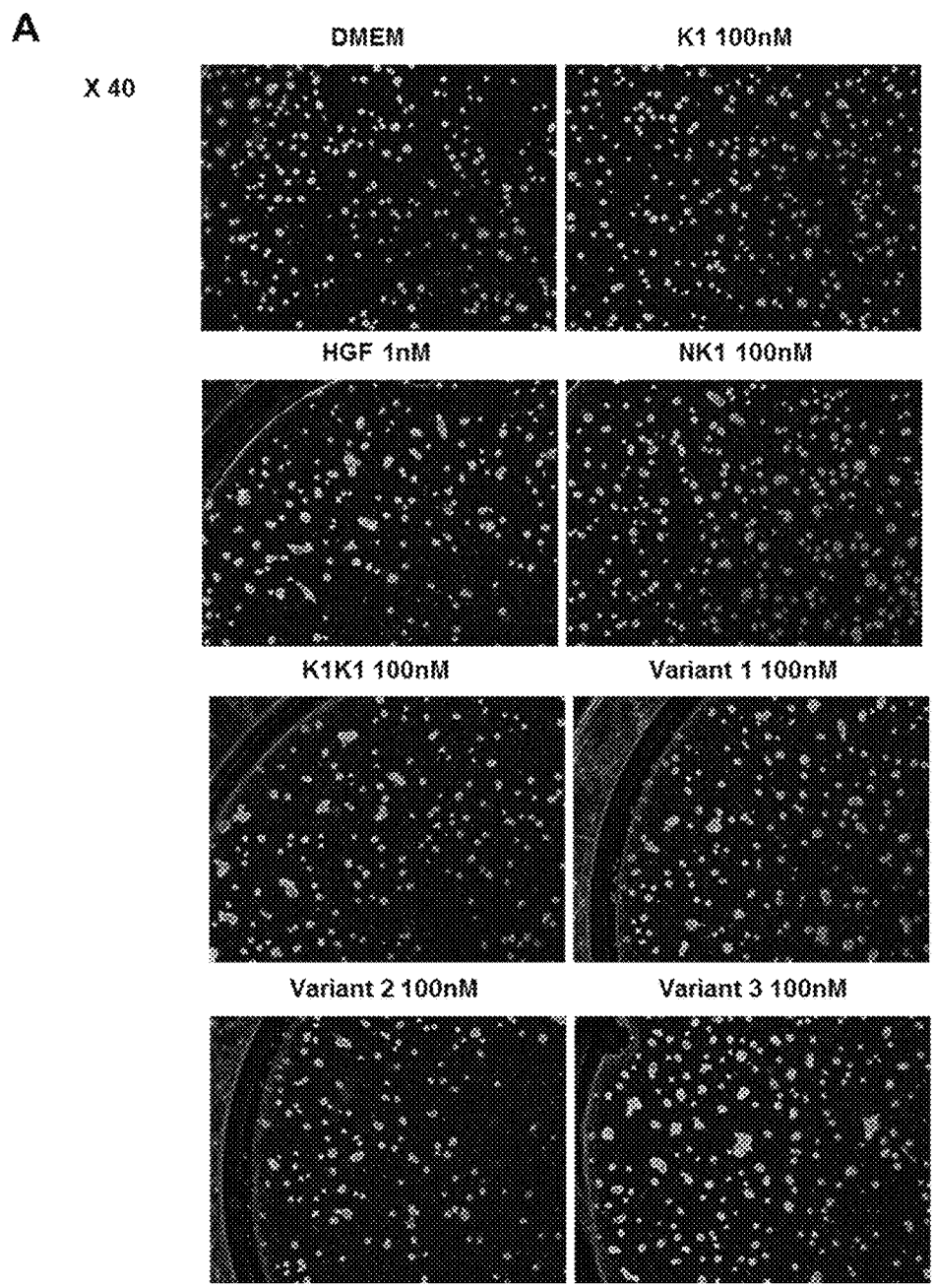
Figure 15:
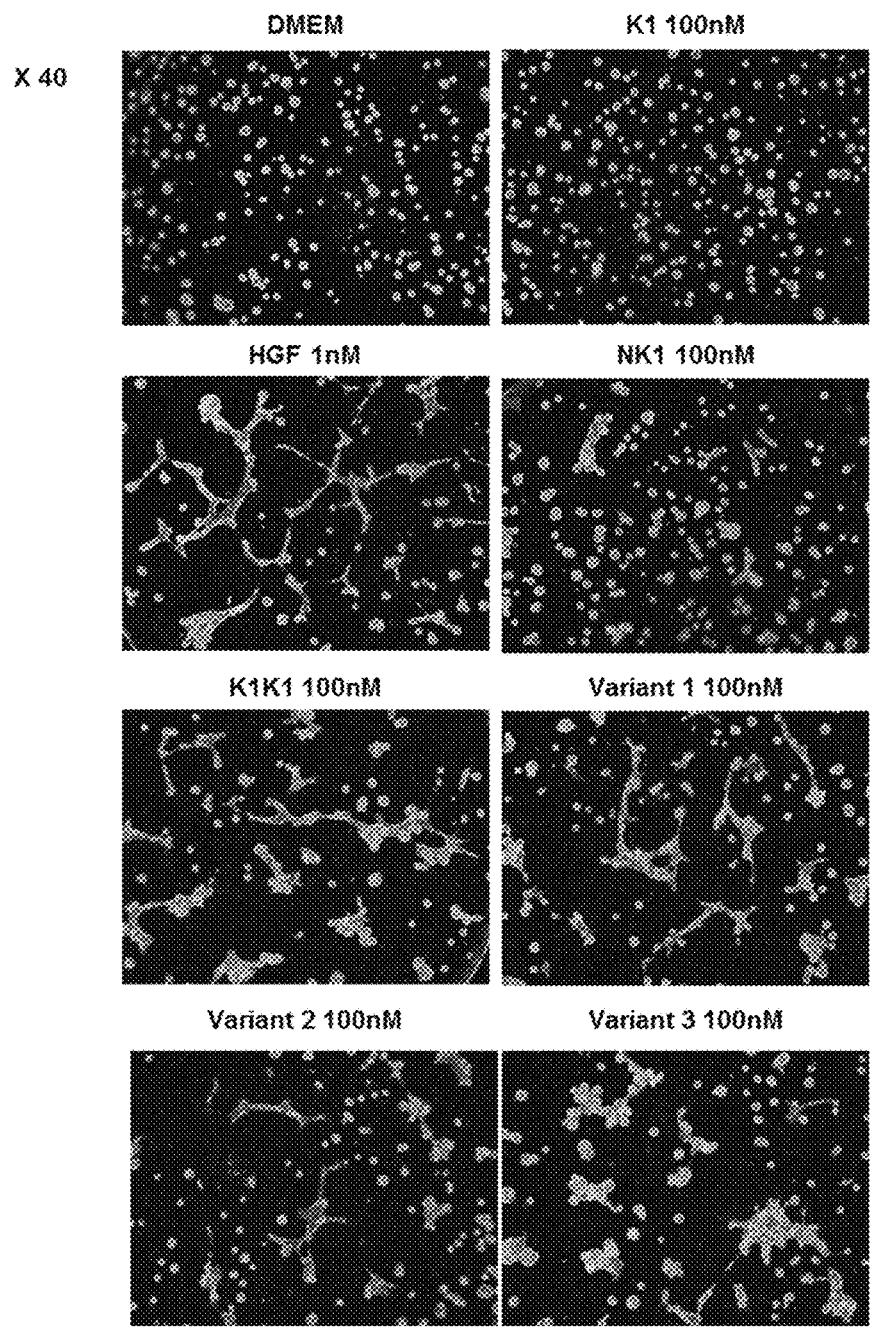
Figure 15:
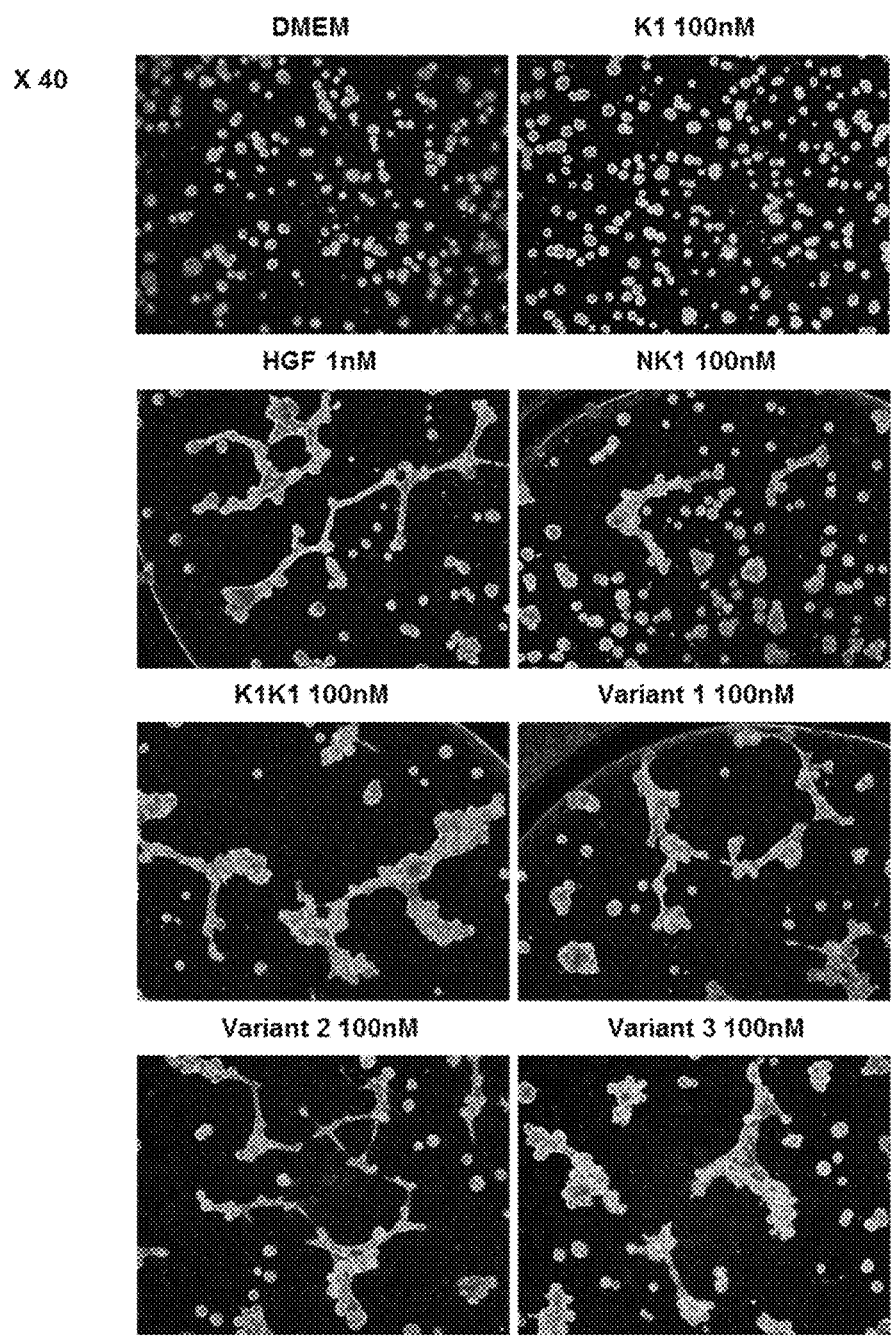

FIG. 15. Cellular phenotypes induced by K1K1 protein (Matrigel™ morphogenesis assay). MDCK cells were seeded onto a layer of Matrigel™ and treated with 1 nM HGF/SF, 100 nM NK1, 100 nM K1K1, variant 1, 2 or 3 and 100 nM K1 monomer. Cells were then observed under a microscope (40×), after one (A), two (B) and three (C) days of culture. Ctrl: DMEM 10% FCS.

Figure 16:
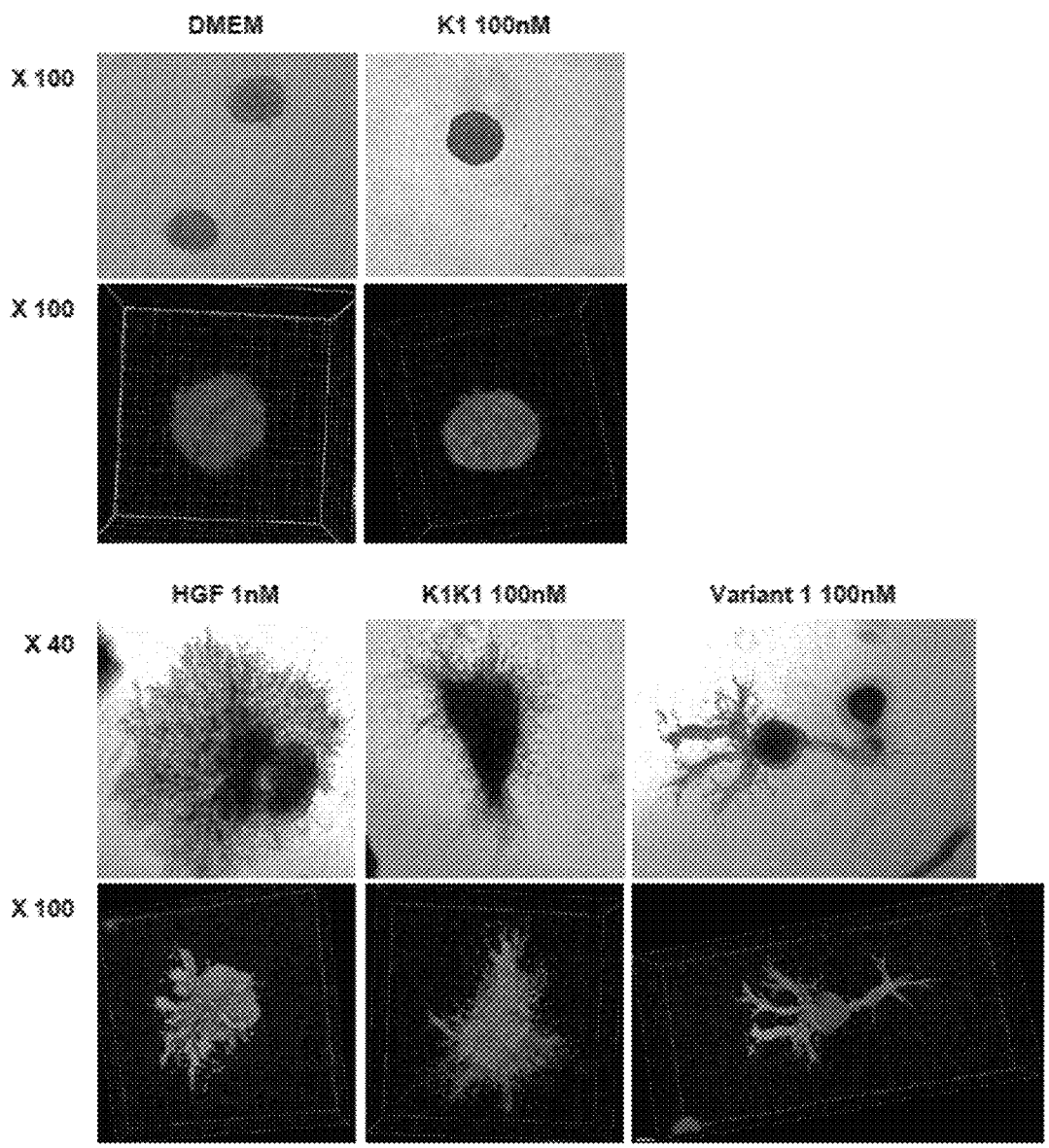

FIG. 16. Cellular phenotypes induced by K1K1 protein (Matrigel™ 3D morphogenesis assay). MDCK cells were seeded into a layer of type 1 collagen-Matrigel™ and culture media containing 1 nM HGF/SF (HGF), 100 nM K1K1, 100 nM K1K1 variant 1 and 100 nM K1 monomer was added onto the layer. Cells were fixed, stained and then observed under a microscope (100×). Ctrl: DMEM 10% FCS.

Figure 17:
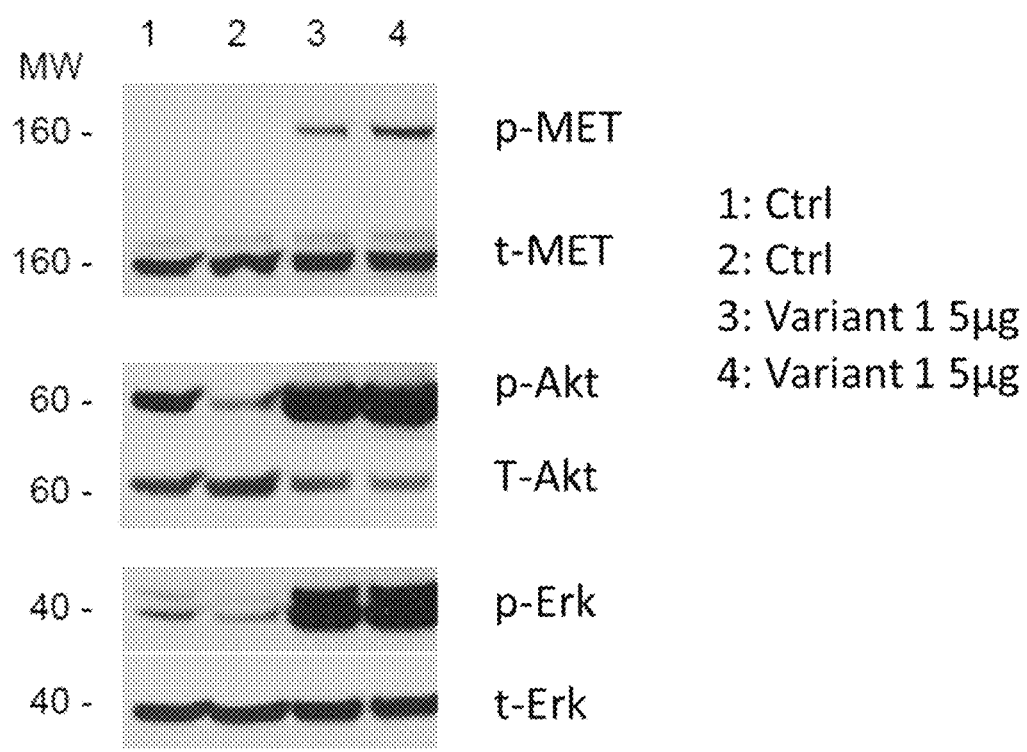

FIG. 17. In vivo MET activation by K1K1 variant 1 (Tagless). Mice were injected (IV) with 5 µg of K1 monomer or 5 µg K1K1 Variant 1. After 10 min, livers were extracted, snap frozen and crushed. MET, Akt and ERK phosphorylation status in cell lysates was analyzed by Western blot.

Figure 18:
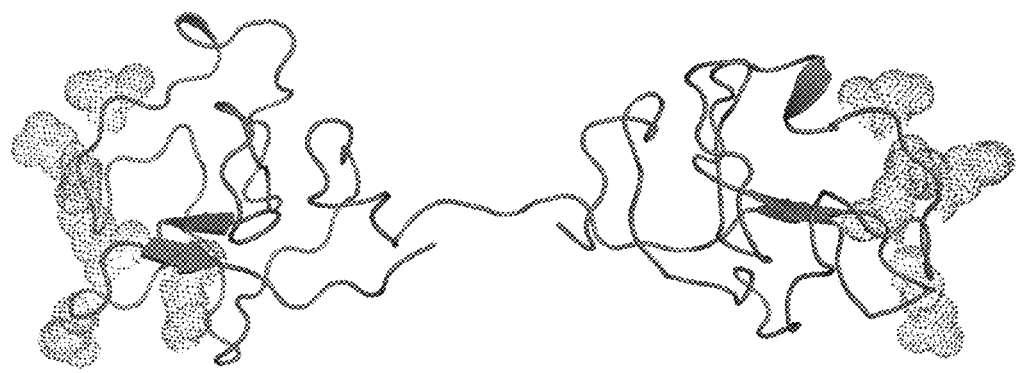
Figure 18:
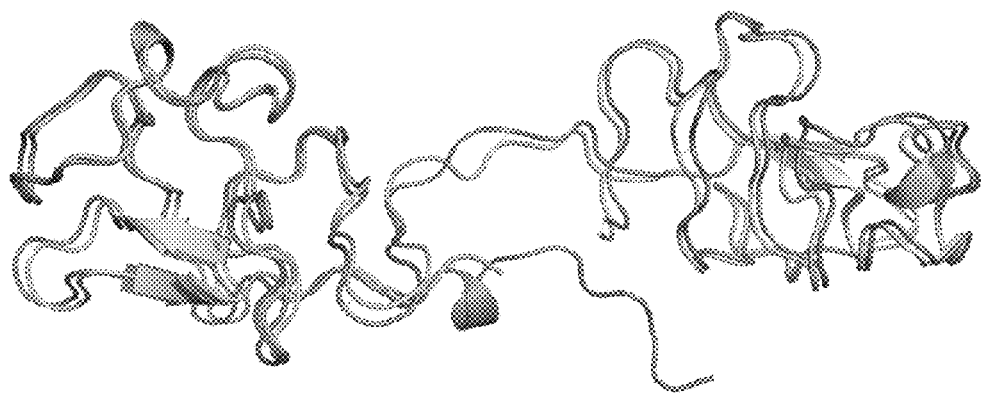

FIG. 18. Crystal structure and molecular alignment of K1K1 and K1K1 variant 1 (Tagless). Crystal structure of K1K1 variant 1 (Tagless) at a resolution of 1.8 Å. The residues known to be responsible for binding the MET receptor are dotted in the figure (A). Structural alignment of K1K1 (A) and K1K1 variant 1 (Tagless) (B). The calculated RMSD value of 0.819 Å is shown in the bottom right corner of the figure (B).

Figure 19:
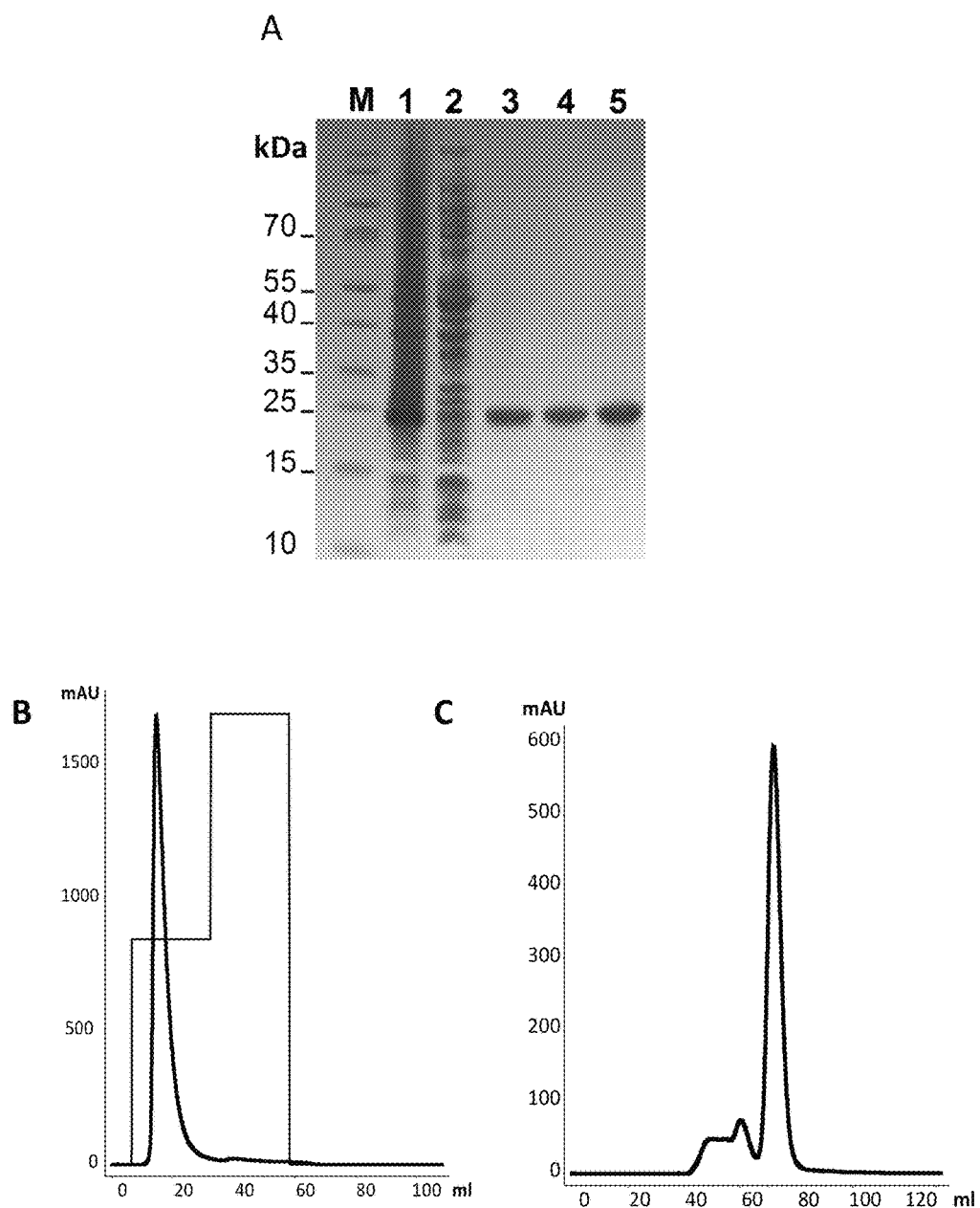

FIG. 19. HisTrap purification of the K1K1 protein from inclusion bodies of E. coli BL21 culture. Reducing SDS-PAGE of bacterial lysates (E. coli, BL21) and the K1K1 protein at different stages of purification. (A) Lane M: molecular weight marker; lane 1: Insoluble crude material after sonication; lane 2: soluble crude material after sonication; lane 3: K1K1 after 72 hours solubilisation in 2 M L-arginine; lane 4: K1K1 after affinity chromatography purification (HisTrap FF 5 ml); lane 5: K1K1 after size exclusion chromatography. (B) HisTrap chromatography of the K1K1 (H6) protein extracted from ncIBsinclusion bodies. (C) Superdex 75 chromatography of the K1K1 (H6) protein extracted from ncIBsinclusion bodies.

Figure 20:
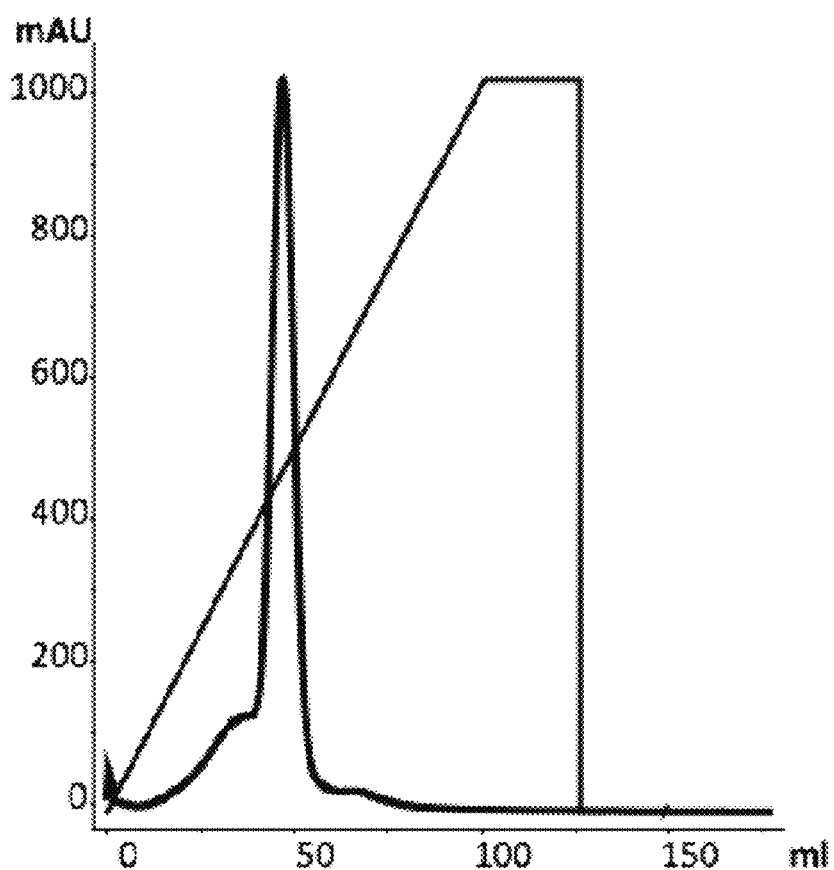

FIG. 20. Affinity chromatography purification of K1K1 variant 1 (Tagless) from inclusion bodies of E. coli BL21 culture (HiTrap™ Heparin HP column). The fractions corresponding to the main protein peak were pooled together and concentrated to a suitable volume for preparative gel filtration chromatography.

Figure 21:
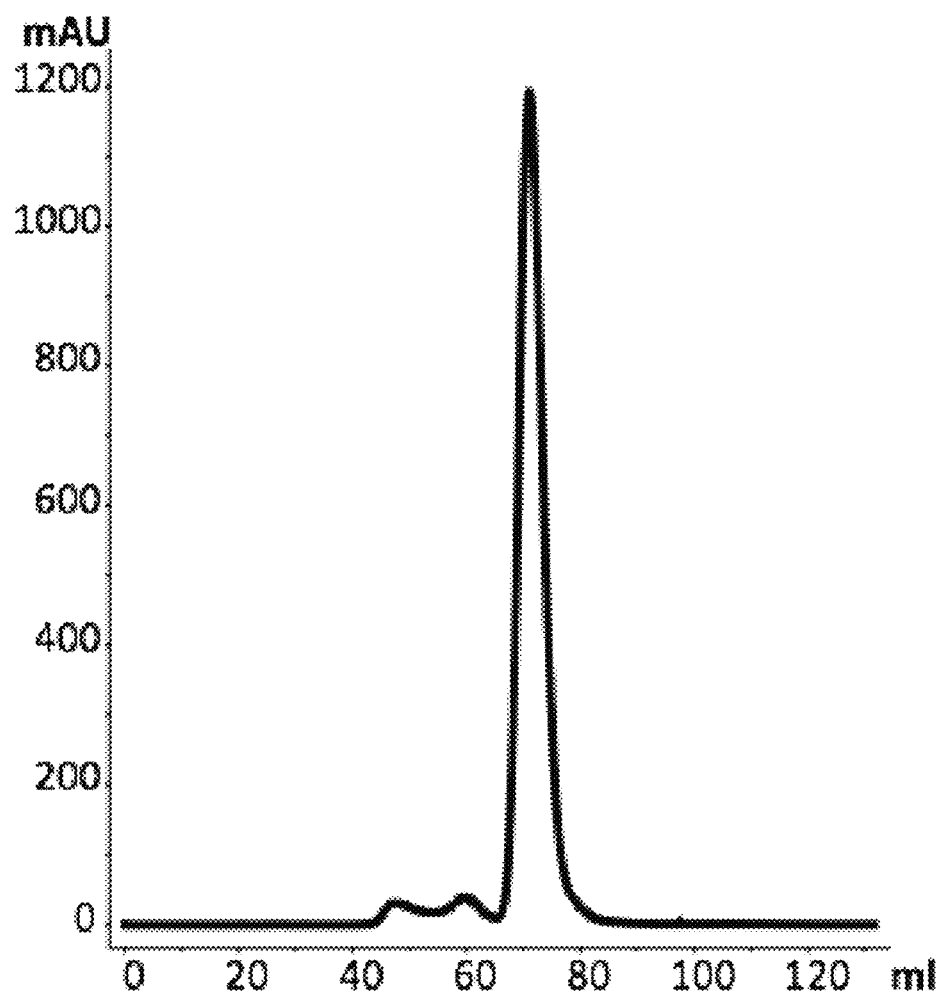

FIG. 21. Size exclusion chromatography of K1K1 variant 1 (Tagless). The fractions corresponding to the main peak from the HiTrap™ Heparin HP column (FIG. 20) were pooled, concentrated and an aliquot was loaded on a Superdex column.

EXAMPLES

Example 1. Production of K1K1 and K1K1 Variants (Tagless)

A prokaryotic expression plasmid (pET45b(+)-K1K1) was constructed by subcloning a DNA fragment containing two tandem repeats of the K1 domain (aa 128-206) of HGF/SF (FIG. 1). A short linker connects the first and second K1 domain. The construct has been designated HGF/SF-K1K1 (abbreviated to K1K1). The prokaryotic expression plasmid was transfected into BL21 (DE3) cells.

After successful transformation, protein production was started and during this phase bacterial cells were grown at 18° C. for 24 h after being induced with a low concentration of IPTG (0.4 mM). After a very gentle extraction procedure inclusion bodies containing K1K1 (or its variants) were resuspended in buffer containing high concentration of L-arginine, incubated at 4° C. for 72 hours in order to solubilize and extract the protein. The extracted protein was then purified by affinity chromatography followed by a gel filtration chromatography step.

A typical elution profile on HisTrap column of a fraction enriched in atypical inclusion bodies and solubilised/renatured with 2 M L-arginine after overnight induction of BL21 cells with 0.4 mM IPTG at 25° C. is shown in FIG. 2. The main peak elutes at ~0.2 M imidazole (FIG. 2a) and contains predominantly the K1K1 protein (FIG. 2b).

The K1K1 protein is not homogeneous. Size exclusion chromatography of the HisTrap pool on Superdex 75 shows three peaks (FIG. 3a). Peak 1 represents minor high molecular weight contaminants readily resolved and not always present in the HisTrap pool. Peaks 2 and 3 are consistently observed and both contain the K1K1 protein. Peak 3 contains the protein with the expected elution volume on Superdex 75 and the expected apparent mass on SDS-PAGE. Peak 2 contains "a dimer of dimer", namely two K1K1 molecules that can be separated from the main K1K1 peak and run slower on SDS-PAGE under non reducing conditions (FIG. 3b) but cannot be distinguished from the main K1K1 protein on reducing gels (FIG. 3c). (Supplementary results are shown in FIG. 19).

The heterogeneity of the HisTrap pool of the K1K1 protein was confirmed by cation exchange chromatography (FIG. 4). The cation exchange column resolves three peaks, of which the main peak (peak 2) has potent biological activity. Peak 1 and peak 3 are biologically inactive.

The other K1K1 variants devoided of the poly-histidine tag were purified through affinity chromatography using a heparin-sepharose affinity chromatography column. A typical HisTrap™ Heparin elution profile of K1K1 variant 1 (Tagless) after solubilization with L-arginine is shown in FIG. 20. The main peak contains highly pure K1K1 variant 1 (Tagless) as shown in the gel filtration chromatogram (FIG. 21).

The protocol based on heparin affinity purification followed by gel filtration is independent of the presence of the His-tag. The heparin allows the purification of properly folded protein while the nickel column is less specific/discriminative. This procotol can be used for all variants.

Example 2. K1K1 is a Potent MET Agonist

Binding ability of K1K1 has been determined by a cross titration ALPHAScreen® assay using recombinant MET-IgG1 chimera (FIG. 6A) and indicates a binding between K1K1 and MET. MET activation and downstream signaling in HeLa cells upon HGF/SF, K1K1, K1B (monomeric biotinylated K1 domain) or recombinant NK1 incubation was analyzed by western blot (FIG. 5) or by ALPHAscreen quantitative approaches (FIG. 6B). Typically, HGF/SF triggered maximal ERK and Akt activation down to pM concentrations. Impressively, K1K1 was able to trigger ERK and Akt phosphorylation levels down to a low nM range, and thus displayed an agonist activity similar to NK1 protein. Moreover, K1K1 induced a strong MET phosphorylation at 100 nM. It was also determined the MET and downstream signaling activation kinetics (0-20 min) using western Blot (FIG. 7). Typically, HGF/SF induced a maximum of MET autophosphorylation between 5 and 10 min, followed by a maximum of Akt and ERK phosphorylation at around 10-20 min. In comparison, MET phosphorylation proceeded much faster with K1K1 and NK1, i.e. within the very first minute, and then decreased. Accordingly, maximum ERK and Akt activation was observed earlier, after only 3-7 min.

Example 3. K1K1 Promotes Cell Scattering, Morphogenesis and Survival Phenotypes

Initial studies on the biological activity of the K1K1 protein have been carried out using the MDCK colony scatter assay and are summarised in FIG. 8. The activity of the HisTrap pools from 7 different expression experiments have been compared with those of native, full length HGF/SF and NK1, a fragment of HGF/SF extensively characterised and a further useful benchmark. The activity of the K1K1 is ~3 fold lower than that of HGF/SF on a molar basis.

In the presence of HGF/SF (100 pM) for 18-24 h, MDCK cells acquired a mesenchymal-like phenotype and scatter. This marked phenotype was also induced by NK1 protein and K1K1 (FIG. 9).

Further cell assays were performed using lumina basal like matrix (Matrigel™) as a mimic of basement extracellular matrix. In these conditions and without treatment, MDCK cells spontaneously form tight spherical clusters on Matrigel™ within 24 h. In contrast, when stimulated with HGF/SF, MDCK cells self-organize into branched and connected structures. Notably, NK1 and K1K1 widely promoted the formation of such structures (FIG. 10).

The capacity of the agonists to promote the survival of cells after apoptotic stress was examined. This phenotype is a hallmark of HGF/SF, which can protect many cell types against death induced by serum depletion, ultra-violet radiation, ischemia or some chemical substances. MDCK cells were stressed using anisomycin, a DNA and protein synthesis inhibitor which induces apoptosis. Anisomycin treatment induced ~90% of cell death after 16 h, but only ~10% of cell death when pretreated with HGF/SF (FIG. 11). Pretreatment with K1K1 and NK1 resulted in ~25% of cell death and therefore also protect the cells to a significant extent.

Example 4. Complementary Results from Other K1K1 Constructs

MET activation and downstream signaling in HeLa cells upon HGF/SF, K1K1 (6×His tag), K1K1 variant 1 (tagless), K1K1 variant 2 (long linker), K1K1 variant 3 (GS linker), or NK1 incubation was analyzed by western blot (FIG. 12) and by ALPHAScreen® quantitative approaches (FIG. 13). Typically, HGF/SF triggered maximal ERK and Akt activation down to pM concentrations. Impressively, K1K1 and its variants were able to trigger ERK and Akt phosphorylation levels down to 100 pM range, and thus displayed an agonist activity at least 10 times more potent than NK1. Moreover, K1K1 and its variants induced a strong MET phosphorylation starting at 100 pM.

In the presence of HGF/SF for 24 h, MDCK cells acquired a mesenchymal-like phenotype and scatter (FIG. 14). This marked phenotype was also induced by K1K1 and variants 1, 2 and 3. K1 monomer has no effect.

Further cell assays were performed using lumina basal like matrix (Matrigel™) as a mimic of basement extracellular matrix. In these conditions and without treatment, MDCK cells spontaneously form tight spherical clusters on Matrigel™ within 24 h. In contrast, when stimulated with HGF/SF, MDCK cells self-organize into branched and connected structures. Notably, K1K1 and its variants widely promoted the formation of such structures (FIG. 15).

Similarly, when cultivated into collagen/Matrigel™ matrix, MDKC cells self-organized in branched structures. Invasiveness and branching of these 3D structures are strongly promoted by HGF. Clearly, K1K1 and variant 1 promote spectacular 3D morphogenesis (FIG. 16).

Finally, K1 monomer or K1K1 variant 1 were injected intravenously to see if it could activate MET and downstream pathways in the liver, an organ well known to strongly express MET receptor. After 10 min, livers were extracted and MET, ERK and Akt phosphorylation status was determined by Western blot (FIG. 17). K1K1 variant 1 injection induced a clear MET phosphorylation associated with a strong Akt and ERK activation in the liver. In contrast, K1 control led to no detectable signal.

Example 5. 3D Structure of K1K1 Variant 1 (Tagless)

The crystal structures of both K1K1 and K1K1 variant 1 (tagless version) were resolved by X-ray crystallography at a resolution of 1.4 and 1.8 Å (Angstrom) respectively. These structures show a very interesting and important fact: in both cases the K1K1 molecule adopts an extended conformation exposing externally and on opposite sides the two MET binding sites (FIG. 18 panel A). This confirms the utility of the creation of a molecule capable of binding two receptors in the correct orientation forming an active signalling complex. From the alignment of the 3D structures of K1K1 and K1K1 variant 1 it appears that they are almost identical, with a RMSD (root-mead square deviation of atomic position) lower than one A (FIG. 18 panel B).

Methods

Vector Construction

A prokaryotic expression plasmid (pET45b(+)-K1K1) was constructed by subcloning a DNA fragment containing two copies of the K1 domain in head to tail (N-ter to C-ter) orientation. The cDNA sequence encoding K1K1 was amplified by PCR from another expression plasmid (pPIC9K-K1K1) produced for expression of K1K1 in the yeast P. pastoris. In order to assemble the expression vector (pET45b(+)-K1K1) the K1K1 cDNA was previously created by the fusion of two human HGF/SF kringle 1 domains, each of them previously amplified by PCR technique. The following set of primers was used in order to amplify the N terminal monomer of K1K1: the forward primer P1 (5'-ATCATCCCATGGCCATTAGAAACTGCATCATTGG-TAAAGGACG-3') (SEQ ID NO: 22) and the reverse primer P3 (5'-TTCAACTTCTGAACACTGAGGA-3') (SEQ ID NO: 20). For the C terminal monomer, the following pair of primers was used: the forward primer P4 (5'-CAGAAGTT-GAATGCATCATTGGTGAAGGA-3') (SEQ ID NO: 21) and the reverse primer P2 (5'-ACAGCGGCCGCTCAT-CAA-3') (SEQ ID NO: 23). In order to allow the fusion of the N terminal and C terminal K1 cDNA's the forward primer P3 and the reverse primer P4 both carry the Hpy188I restriction site. In the following pair of primers, the forward primer P1 (5'-ATCATCCCATGGCCATTAGAAACTG-CATCATTGGTAAAGGACG-3') (SEQ ID NO: 22) and the reverse primer P2 (5'-ACAGCGGCCGCTCATCAA-3') (SEQ ID NO: 23), carry NcoI and NotI sites respectively in order to allow the insertion of the K1K1 cDNA into the expression vector. PCR conditions consisted in 28 cycles of 94° C. for 15 secondes, 54° C. for 30 secondes, and 68° C. for 60 secondes, and the enzyme used for DNA amplification was the Platinum® Pfx DNA Polymerase (Invitrogen). The PCR amplified DNA fragment was separated on 1.5% agarose gels containing ethidium bromide (EB) and visualised under (long wave length) UV light illumination. The band was recovered and purified from the agarose gel using Zymoclean™ Gel DNA Recovery Kit (Zymogen) and digested using NcoI (New England Biolabs) and NotI (New England Biolabs). The pET45b(+) plasmid was restricted with NcoI and NotI, dephosphorylated and isolated from a 1% agarose gel. The products of digestion were recovered and purified from agarose gel using DNA Clean & Concentrator™ kit (Zymogen) and successively the K1K1 cDNA was inserted in the open vector using Quick ligase kit (New England Biolabs). Ligation product was transformed in E. coli MACH1 cells (New England Biolabs) and bacteria were grown over night on LB agar plate containing ampicillin. Single colonies were screened by PCR using a T7 universal forward primer (5'-TAATACGACTCACTATAGGG-3') (SEQ ID NO: 24) annealing and primer P2 (SEQ ID NO: 23) as a reverse primer. Confirmation of the correct orientation of the kringle domains in the K1K1 constructs and absence of artifactual mutations were confirmed by sequencing of the whole construct on both strands.

E. coli Expression

The K1K1 protein and its variants contain a total of 6 disulphide bond (3 in each kringle domain). Production of disulphide-rich proteins in E. coli presents significant challenges and, in the majority of cases, such proteins accumulate in large aggregates called inclusion bodies. Typical inclusion bodies have a diameter of 0.5-1.3 µm and are found inside the bacterial cytoplasm or in the periplasmm.

The inclusion bodies are composed predominantly of the target protein (from 50 up to 90%) although other cytoplasmatic proteins and other cellular constituents are nearly invariably associated with them. Inclusion bodies, however, may also contain correctly folded, target protein, especially when cultures are grown at low temperature. These "non-classical" inclusion bodies are rich in correctly folded precursor of the target protein, which can be extracted effectively under non-denaturing conditions.

This latter strategy has been adopted here in order to express correctly folded and biologically active K1K1. Briefly, the plasmid pET45b(+)-K1K1 was used to transform the DH5a strain of E. coli (for propagation) and the BL21 strain (for expression). BL21 cells were cultured in LB medium containing ampicillin at 37° C. until the cells reached an OD600 between 0.5 and 0.6, at which point expression was induced with 0.4 mM Isopropyl β-D-1-thiogalactopyranoside (IPTG). After induction, cells were grown for 24 hours at 18° C. in a shacking incubator (250 rpm). The cells were harvested by centrifugation at 5,000 g for 30 min at 4° C., resuspended in PBS and lysed by sonication (10 cycles of 20 seconds at 40 sec intervals). Alternatively, cells were lysed using lysozyme at 37° C. for 1 h followed by several cycles of freezing and thawing or mechanical lysis using Emulsyflex. After sonication or lysozyme treatment the cell lysate was centrifuged at 5,000 g for 30 min at 4° C., resuspended in PBS containing 0.4% (v/v) of Triton X-100 and incubated for 1 h at room temperature with gentle stirring to remove nonspecifically adsorbed proteins. The lysate was centrifuged again at 5,000 g for 30 minutes at 4° C., the pellet resuspended in PBS containing 0.025% (v/v) phenoxypolyethoxylethanol (NP40) and incubated for 1 h at 4° C. with gentle stirring in order to remove additional non-specifically adsorbed proteins followed by a new centrifugation. Finally, the pellet washed several times in ice-cold PBS in order to remove traces of detergent. For solubilisation and renaturation of the K1K1 protein with L-arginine, the pellet obtained, consisting of almost pure inclusion bodies, was resuspended in PBS containing 2 M L-arginine and incubated overnight at 37° C. shacking at 250 rpm.

Affinity Chromatography

The supernatant obtained after overnight incubation with 2 M L-arginine and a further centrifugation step (5,000 g for 30 min at 4° C.) was filtered through a 0.22 μm filter and loaded on a 1 ml HisTrap crude FF affinity column equilibrated in PBS adjusted to 500 mM NaCl at 2 ml/min. The column was washed until the baseline returned to zero and bound proteins eluted with a 130 ml gradient of imidazole (0-500 mM) in PBS adjusted to 500 mM NaCl. Protein-containing fractions were analysed by SDS-PAGE, size exclusion chromatography on a Superdex 75 10/30 (GE Healthcare) column and for biological activity using the MDCK colony scatter assay (Stoker, M. et al., Scatter factor is a fibroblast-derived modulator of epithelial cell mobility. Nature 327, 239-242 (1987)). Alternatively, the supernatant obtained after 72 hours incubation with 2 M L-arginine and further centrifugation step (15,000 g for 30 min at 4° C.) was diluted 100 times into loading buffer (25 mM Tris pH 7.4, 500 mM NaCl) and filtered through a 0.22 μm filter.

The sample prepared in this way was loaded onto the column (5 ml HisTrap™-FF) at a flow rate of 1.5 ml/min overnight. The column was washed until the recorded UV trace showed a flat low absorbance baseline. Bound material was then eluted at 5 ml/min with a step-gradient elution using 50% buffer B (25 mM Tris, pH 7.4, 500 mM NaCl 1 M imidazole) over 10 column volumes, then reaching 100% buffer B in one step and holding it for another 10 column volumes. The UV absorption was monitored at 280 nm and fractions of 5 ml were collected throughout the whole elution procedure.

Gel Filtration Chromatography

A HiLoad™ 16/60 Superdex™ 75 was equilibrated with column buffer (25 mM Tris, 500 mM NaCl, pH 7.4). The concentrated fractions from the affinity chromatography step were loaded on to the column using a 5 ml loop. The chromatographic run was performed at a flow rate of 0.5 ml/min and 5 ml fractions were collected throughout the whole elution procedure. The fractions corresponding to the expected peak were collected, pooled together, analysed and if necessary flash frozen for storage at −80° C.

Cation Exchange Chromatography

Soluble variant 1 protein from inclusion bodies and the protein containing fractions from the His-Trap column (K1K1, variant 2 and variant 3) were pooled and dialysed against 50 mM MES, 150 mM NaCl pH 6.0 for 24 hours at 4° C. Samples were centrifuged, filtered through a 0.22 μm filter and loaded at 0.5 ml/min on a 1 ml Resource-S column (GE Healthcare) equilibrated in 50 mM MES, 150 mM NaCl pH 6.0. Bound proteins were eluted with a gradient of NaCl (0.25-100 M). Fractions collected and analysed by SDS-PAGE and MDCK colony scatter assay.

MET Signaling Pathway and Dose Response (Western Blot)

HeLa cells were treated with 500 pM HGF, 1 nM K1K1, 1 nM K1K1 variant 1, 2, and 3 or 1 or 100 nM NK1 for 10 min. Cell lysates were then analyzed by specific total MET, Akt and ERK or phospho-MET, phospho-Akt and phospho-ERK western blot. Cells were collected by scraping and then lysed on ice with a lysis buffer (20 mM HEPES pH 7.4, 142 mM KCl, 5 mM MgCl2, 1 mM EDTA, 5% glycerol, 1% NP40 and 0.1% SDS) supplemented with freshly added protease and phosphatase inhibitors (Sigma). Lysates were clarified by centrifugation (20,000 g×15 min) and protein concentration was determined (BCA protein assay Kit, Pierce®, Thermo scientific, IL, USA). The same protein amount of cell extracts was separated by either classical SDS-PAGE or NuPAGE (4-12% or 10% Bis-Tris precast gels) (Life technologies) and electrotransferred to polyvinylidene difluoride (PVDF) membranes (Merck Millipore). Membranes were probed with indicated primary antibodies, followed by incubation with appropriate HRP conjugated secondary antibodies. Protein-antibody complexes were visualized by chemiluminescence with the SuperSignal® West Dura Extended Duration Substrate X-ray films (CL-Xposure™ Film, Thermo scientific).

For dose response, HeLa cells were treated with 10, 100, and 500 pM HGF/SF (HGF), 100, 500, and 1000 pM K1K1 variant 1 and 100, 500, and 1000 pM K1K1 for 10 min.

Kinetic (Western Blot)

HeLa cells were treated with 100 pM HGF, 100 nM K1K1 and 100 nM NK1, for 1, 5, 10, or 20 min. Cell lysates were then analyzed by specific total MET, Aid and ERK or phospho-MET, phospho-Akt and phospho-ERK western blot. Cells were collected by scraping and then lysed on ice with a lysis buffer (20 mM HEPES pH 7.4, 142 mM KCl, 5 mM MgCl2, 1 mM EDTA, 5% glycerol, 1% NP40 and 0.1% SDS) supplemented with freshly added protease and phosphatase inhibitors (Sigma). Lysates were clarified by centrifugation (20,000 g×15 min) and protein concentration was determined (BCA protein assay Kit, Pierce®, Thermo scientific, IL, USA). The same protein amount of cell extracts was separated by either classical SDS-PAGE or NuPAGE (4-12% or 10% Bis-Tris precast gels) (Life technologies) and electrotransferred to polyvinylidene difluoride (PVDF)

membranes (Merck Millipore). Membranes were probed with indicated primary antibodies, followed by incubation with appropriate HRP conjugated secondary antibodies. Protein-antibody complexes were visualized by chemiluminescence with the SuperSignal® West Dura Extended Duration Substrate (Thermo scientific), using X-ray films (CL-Xposure™ Film, Thermo scientific).

MDCK Scattering

MDCK isolated cell islets were incubated for 18-24 h in culture media with 100 pM HGF/SF, 100 nM K1K1 and 100 nM NK1. Alternatively, MDCK isolated cell islets were incubated for 24 h in culture media with 500 pM HGF/SF, 10 nM K1K1 and variant 1, 2 or 3 and 100 nM K1 monomer. Cells were then stained and observed under a microscope (100×).

Cells were seeded at low density (2,000 cells/well in a 12-well plate) to form compact colonies. After treatment, when colony dispersion was observed, the cells were fixed and colored by Hemacolor® stain (Merck, Darmstadt, Germany) according to the manufacturer's instructions. Representative images were captured using a phase contrast microscope with 100× magnification (Nikon Eclipse TS100, Tokyo, Japan).

MDCK Morphogenesis

MDCK cells were seeded onto a layer of Growth Factor Reduced Matrigel™ (BD Biosciences) (100,000 cells/well of a 24-well plate), treated for 18-24 h with 100 pM HGF/SF, 100 nM K1K1 and 100 nM NK1, and observed under a phase contrast microscope. Representative images were captured with 40× and 100× magnification (Nikon Eclipse TS100).

Alternatively, MDCK cells were seeded onto a 10 µL layer of Growth Factor Reduced Matrigel™ (BD Biosciences) into 15 wells Ibidi® microslide angiogenesis (2,500 cells/well), and treated with 50 µL of 1 nM HGF/SF, 100 nM K1K1, variant 1, 2 or 3 and 100 nM K1 monomer Cells were then observed at 24, 48 and 72 h (40×) under a phase contrast microscope. Representative images were captured with 40× magnification (Nikon Eclipse TS100).

MDCK 3D Morphogenesis

MDCK cells were seeded into a thick layer of type 1 collagen-Matrigel™ in a 24 well plate covered by culture media containing 1 nM HGF/SF (HGF), 100 nM NK1, 100 nM K1K1, variant 1 and 100 nM K1 monomer. Cells were fixed, stained with Evans Blue (0.01%) and then observed under a contrast (Nikon Eclipse TS100) and confocal (Leica LSM 880) microscope (Ex405 nm/Em630). Representative images were captured with 40× or 100× magnification and 3D reconstituted in Z-stack.

MDCK Survival

MDCK cells were cultured overnight (15 h) in medium containing 0.1% FBS with or without anisomycin (0.7 µM) and in the presence of 500 pM HGF/SF, 100 nM K1K1 and 100 nM NK1. An MTT assay was then performed to evaluate cell survival. Results are expressed as the percentage of untreated control.

Cells were washed with PBS to eliminate dead cells and then incubated in medium containing 0.5 mg/ml 3-(4,5-dimethylthiazol-2-yl)-2,5-diphenyltetrazolium bromide (MTT, Invitrogen) for 1 h. After a washing step with PBS, the formazan crystals were solubilized and mixed thoroughly with 0.04 M HCl in isopropanol. For each condition, 60 µl of formazan solution was loaded in triplicate onto a 96-well plate. Absorbance was then measured with a microplate spectrophotometer at 550 nm and 620 nm, as test and reference wavelengths, respectively. The absorbance correlates with cell number.

Cross Titration Assay

Cross-titration assays for binding of K1K1 to recombinant MET-Fc protein were performed in 384-well microtiter plates (OptiPlate™-384, PerkinElmer©, CA, USA, 50 µL of final reaction volume). Final concentrations were 0-300 nM for K1K1, 0-10 nM for MET-Fc, 10 µg/mL for streptavidin coated donor beads and protein A-conjugated acceptor beads. The buffer used for preparing all protein solutions and the bead suspensions was: PBS, 5 mM HEPES pH 7.4, 0.1% BSA. The plate was incubated at 23° C. for 60 min in a dark box. The emitted signal intensity was measured using standard Alpha settings on an EnSpire® Multimode Plate Reader (PerkinElmer).

Akt and ERK Phosphorylation Assay by ALPHAScreen® SureFire® Ultra™ Method

The assay was performed according to the manufacturer's protocol mentioned in ALPHAScreen® SureFire® Ultra™ (PerkinElmer©, CA, USA). Briefly, cells were plated, stimulated for 7 min with different agonists (HGF/SF, NK1, K1K1 and K1B (biotinylatedK1)), and then lysed in the same 96-well culture plate. Lysates (10 µL) were transferred to 384-well microplates for the detection of phosphorylated Akt (ALSU-PAKT-B500, Ser473) and ERK (ALSU-PERK-A500, Thr202/Tyr204). ALPHAScreen® SureFire® Ultra™ acceptor and donor beads were added and incubated for 2 hours. The emitted signal intensity was measured using standard Alpha settings on an EnSpire® Multimode Plate Reader (PerkinElmer).

Akt and ERK Phosphorylation Assay by ALPHAScreen SureFire® Method

The assay was performed according to the manufacturer's protocol mentioned in ALPHAScreen® SureFire® ERK (TGRES500) and Akt (TGRA4S500) (PerkinElmer©, CA, USA). Briefly, cells were plated, stimulated for 10 min with different agonists (HGF/SF, NK1, K1K1, Variant 1, 2 or 3 and K1 (biotinylatedK1)), and then lysed in the same 96-well culture plate. Lysates (5 µL) were transferred to 384-well microplates for the detection of phosphorylated Akt (Ser473) and ERK (Thr202/Tyr204). ALPHAScreen® SureFire® acceptor and donor beads mixtures were added and incubated for 2 hours according to manufacturer procedure. The emitted signal intensity was measured using standard Alpha settings on an EnSpire® Multimode Plate Reader (PerkinElmer).

In vivo MET Signaling Activation:

To visualize MET activation in the liver FVB mice (n=2) weighing 19-21 g (Charles River) were used. After anesthesia with isoflurane (Aerrane, Baxter, USA), mice were given intravenous injections of 5 µg of K1 monomer or K1K1 variant 1 in PBS. The mice were sacrificed after 10 minutes, and livers perfused with PBS supplemented with protease and phosphatase inhibitors. Livers were extracted and analyzed by Western Blot for MET, ERK and Akt activation.

Fas Induced Fulminant Hepatitis

FVB mice weighing 19-21 g are used for this experiment. After anesthesia with isoflurane, mice are given intravenous injections of 125 ng/g body weight of anti-Fas antibody (Clone Jo-2, CD95, Pharmingen, BD Biosciences) mixed with different agonists such as K1K1 variant 1 (Tagless), HGF/SF, NK1. The mice are injected a second time with each agonist 90 min after the first injection. The mice are sacrificed after 3 additional hours, and their livers perfused with PBS supplemented with protease and phosphatase inhibitors.

In parallel, to visualize MET activation in the liver, mice are given intravenous injections of each agonist for 10 min.

For histological analysis, liver tissue is collected, fixed overnight in 4% paraformaldehyde, and snap frozen in isopentane, submerged in liquid nitrogen, and embedded in OCT (Tissue-Tek®, VWR, PA, USA). Frozen liver sections (5 μm) are stained with hematoxylin and eosin (HE) for general morphology. TUNEL staining for apoptosis is also performed on liver sections according to the manufacturer's instructions (Apoptag® Fluorescein Direct In Situ kit, Merck Millipore, Billerica, Mass., USA). For molecular analysis, extracted liver tissue is immediately frozen in liquid nitrogen. Livers are crushed in lysis buffer supplemented with freshly added protease and phosphatase inhibitors.

In Vivo «Wound Healing» Experimental Protocol

The animal model is a pork (3 porks for the study).

The accommodation comprises 7 days of acclimatization+25 days of following-up.

The clinical observations and weighing are made once a week during 4 weeks.

Wound-Healing Model:
Squarred Dermo-epidermal wounds (2×2 cm) are made on the two sides of the animal.
Each animal is its own witness
  First side=treated with the formulation
  Second side=negative control, treated with placebo
Treatment: 2 formulations of K1K1 TL (TagLess) at two concentrations (1 and 50 nM)
  Twice a week during 4 weeks
Clinical Observations and Weighing:
Wound-Healing Assessment after Study of the Following Parameters:
  Wound closure—morphometric studies (pictures of wounds)
  Histological biopsies (HES and MTG)—angiogenesis—granulation tissue
  Epithelialization at D7, D14 and D35
Euthanasia.

The invention claimed is:

1. A fusion protein comprising a $K1_a$ peptide domain fused to a $K1_b$ peptide domain wherein both $K1_a$ and $K1_b$ peptide domains consist of a sequence at least 90% identical to SEQ ID NO: 1, wherein the domains are directly linked or linked through a linker of 1 to 20 amino acids and wherein said fusion protein induces activation of the tyrosine kinase receptor MET.

2. The fusion protein according to claim 1, wherein said peptide domains $K1_a$ and $K1_b$ are identical.

3. The fusion protein according to claim 1, wherein each of said peptide domains $K1_a$ and $K1_b$ consists of an amino acid sequence selected from the amino sequences SEQ ID NO: 1 and SEQ ID NO: 2.

4. The fusion protein according to claim 1, wherein the domains are linked through a linker of 1 to 20 amino acids.

5. The fusion protein according to claim 1, wherein the domains are linked through a linker of 10 to 20 amino acids.

6. A nucleic acid molecule encoding the fusion protein of claim 1.

7. A composition comprising the nucleic acid molecule of claim 6 and a pharmaceutically acceptable vehicle.

8. The nucleic acid molecule of claim 6 consisting of the nucleic acid sequence SEQ ID NO: 10.

9. An expression vector containing a nucleic acid molecule of claim 6.

10. A composition comprising the expression vector of claim 9 and a pharmaceutically acceptable vehicle.

11. The expression vector of claim 9 comprising or consisting of SEQ ID NO: 11.

12. An host cell containing the expression vector as claimed in claim 9, wherein the host cell is selected from the group consisting of yeast cells and bacterial cells.

13. A composition comprising the host cell of claim 12 and a pharmaceutically acceptable vehicle.

14. A method for producing a fusion polypeptide comprising culturing the host cell of claim 12 under conditions suitable for expression followed by extracting and purifying the fusion protein.

15. A composition comprising the fusion protein of claim 1 and a pharmaceutically acceptable vehicle.

16. A fusion protein comprising or consisting of an amino acid sequence SEQ ID NO: 7 or an amino acid sequence with at least 90% identity to SEQ ID NO: 7.

* * * * *

```
                        SEQUENCE LISTING

<160> NUMBER OF SEQ ID NOS: 24

<210> SEQ ID NO 1
<211> LENGTH: 79
<212> TYPE: PRT
<213> ORGANISM: Homo sapiens

<400> SEQUENCE: 1

Cys Ile Ile Gly Lys Gly Arg Ser Tyr Lys Gly Thr Val Ser Ile Thr
1               5                   10                  15

Lys Ser Gly Ile Lys Cys Gln Pro Trp Ser Ser Met Ile Pro His Glu
            20                  25                  30

His Ser Phe Leu Pro Ser Ser Tyr Arg Gly Lys Asp Leu Gln Glu Asn
        35                  40                  45

Tyr Cys Arg Asn Pro Arg Gly Glu Glu Gly Gly Pro Trp Cys Phe Thr
    50                  55                  60

Ser Asn Pro Glu Val Arg Tyr Glu Val Cys Asp Ile Pro Gln Cys
65                  70                  75

<210> SEQ ID NO 2
<211> LENGTH: 74
<212> TYPE: PRT
<213> ORGANISM: Homo sapiens

<400> SEQUENCE: 2

Cys Ile Ile Gly Lys Gly Arg Ser Tyr Lys Gly Thr Val Ser Ile Thr
1               5                   10                  15

Lys Ser Gly Ile Lys Cys Gln Pro Trp Ser Ser Met Ile Pro His Glu
            20                  25                  30

His Ser Tyr Arg Gly Lys Asp Leu Gln Glu Asn Tyr Cys Arg Asn Pro
        35                  40                  45

Arg Gly Glu Glu Gly Gly Pro Trp Cys Phe Thr Ser Asn Pro Glu Val
    50                  55                  60

Arg Tyr Glu Val Cys Asp Ile Pro Gln Cys
65                  70

<210> SEQ ID NO 3
<211> LENGTH: 238
<212> TYPE: DNA
<213> ORGANISM: Homo sapiens

<400> SEQUENCE: 3
```

```
tgcatcattg gtaaaggacg cagctacaag ggaacagtat ctatcactaa gagtggcatc    60
aaatgtcagc cctggagttc catgatacca cacgaacaca gcttttttgcc ttcgagctat  120 cggggtaaag acctacagga aaactactgt cgaaatcctc gaggggaaga agggggaccc   180
tggtgtttca caagcaatcc agaggtacgc tacgaggtct gtgacattcc tcagtgtt    238

<210> SEQ ID NO 4
<211> LENGTH: 223
<212> TYPE: DNA
<213> ORGANISM: Homo sapiens

<400> SEQUENCE: 4
tgcatcattg gtaaaggacg cagctacaag ggaacagtat ctatcactaa gagtggcatc    60
aaatgtcagc cctggagttc catgatacca cacgaacaca gctatcgggg taaagaccta  120
caggaaaact actgtcgaaa tcctcgaggg gaagaagggg gaccctggtg tttcacaagc  180
aatccagagg tacgctacga ggtctgtgac attcctcagt gtt                    223

<210> SEQ ID NO 5
<211> LENGTH: 4
<212> TYPE: PRT
<213> ORGANISM: Artificial sequence
<220> FEATURE:
<223> OTHER INFORMATION: peptide sequence of the linker

<400> SEQUENCE: 5

Ser Glu Val Glu
1

<210> SEQ ID NO 6
<211> LENGTH: 12
<212> TYPE: DNA
<213> ORGANISM: Artificial sequence
<220> FEATURE:
<223> OTHER INFORMATION: nucleotide sequence of the linker

<400> SEQUENCE: 6
tcagaagttg aa                                                        12

<210> SEQ ID NO 7
<211> LENGTH: 162
<212> TYPE: PRT
<213> ORGANISM: Artificial sequence
<220> FEATURE:
<223> OTHER INFORMATION: K1K1

<400> SEQUENCE: 7

Cys Ile Ile Gly Lys Gly Arg Ser Tyr Lys Gly Thr Val Ser Ile Thr
1               5                   10                  15

Lys Ser Gly Ile Lys Cys Gln Pro Trp Ser Ser Met Ile Pro His Glu
            20                  25                  30

His Ser Phe Leu Pro Ser Ser Tyr Arg Gly Lys Asp Leu Gln Glu Asn
        35                  40                  45

Tyr Cys Arg Asn Pro Arg Gly Glu Glu Gly Gly Pro Trp Cys Phe Thr
    50                  55                  60

Ser Asn Pro Glu Val Arg Tyr Glu Val Cys Asp Ile Pro Gln Cys Ser
65                  70                  75                  80

Glu Val Glu Cys Ile Ile Gly Lys Gly Arg Ser Tyr Lys Gly Thr Val
                85                  90                  95

Ser Ile Thr Lys Ser Gly Ile Lys Cys Gln Pro Trp Ser Ser Met Ile
```

```
                    100                 105                 110
Pro His Glu His Ser Phe Leu Pro Ser Ser Tyr Arg Gly Lys Asp Leu
            115                 120                 125

Gln Glu Asn Tyr Cys Arg Asn Pro Arg Gly Glu Glu Gly Gly Pro Trp
            130                 135                 140

Cys Phe Thr Ser Asn Pro Glu Val Arg Tyr Glu Val Cys Asp Ile Pro
145                 150                 155                 160

Gln Cys
```

<210> SEQ ID NO 8
<211> LENGTH: 152
<212> TYPE: PRT
<213> ORGANISM: Artificial sequence
<220> FEATURE:
<223> OTHER INFORMATION: K1K1

<400> SEQUENCE: 8

```
Cys Ile Ile Gly Lys Gly Arg Ser Tyr Lys Gly Thr Val Ser Ile Thr
1               5                   10                  15

Lys Ser Gly Ile Lys Cys Gln Pro Trp Ser Ser Met Ile Pro His Glu
            20                  25                  30

His Ser Tyr Arg Gly Lys Asp Leu Gln Glu Asn Tyr Cys Arg Asn Pro
        35                  40                  45

Arg Gly Glu Glu Gly Gly Pro Trp Cys Phe Thr Ser Asn Pro Glu Val
50                  55                  60

Arg Tyr Glu Val Cys Asp Ile Pro Gln Cys Ser Glu Val Glu Cys Ile
65                  70                  75                  80

Ile Gly Lys Gly Arg Ser Tyr Lys Gly Thr Val Ser Ile Thr Lys Ser
                85                  90                  95

Gly Ile Lys Cys Gln Pro Trp Ser Ser Met Ile Pro His Glu His Ser
            100                 105                 110

Tyr Arg Gly Lys Asp Leu Gln Glu Asn Tyr Cys Arg Asn Pro Arg Gly
        115                 120                 125

Glu Glu Gly Gly Pro Trp Cys Phe Thr Ser Asn Pro Glu Val Arg Tyr
    130                 135                 140

Glu Val Cys Asp Ile Pro Gln Cys
145                 150
```

<210> SEQ ID NO 9
<211> LENGTH: 177
<212> TYPE: PRT
<213> ORGANISM: Artificial sequence
<220> FEATURE:
<223> OTHER INFORMATION: K1K1

<400> SEQUENCE: 9

```
Met Ala Ile Arg Asn Cys Ile Ile Gly Lys Gly Arg Ser Tyr Lys Gly
1               5                   10                  15

Thr Val Ser Ile Thr Lys Ser Gly Ile Lys Cys Gln Pro Trp Ser Ser
            20                  25                  30

Met Ile Pro His Glu His Ser Phe Leu Pro Ser Ser Tyr Arg Gly Lys
        35                  40                  45

Asp Leu Gln Glu Asn Tyr Cys Arg Asn Pro Arg Gly Glu Glu Gly Gly
    50                  55                  60

Pro Trp Cys Phe Thr Ser Asn Pro Glu Val Arg Tyr Glu Val Cys Asp
65                  70                  75                  80

Ile Pro Gln Cys Ser Glu Val Glu Cys Ile Ile Gly Lys Gly Arg Ser
```

```
                        85                  90                  95
Tyr Lys Gly Thr Val Ser Ile Thr Lys Ser Gly Ile Lys Cys Gln Pro
                100                 105                 110

Trp Ser Ser Met Ile Pro His Glu His Ser Phe Leu Pro Ser Ser Tyr
            115                 120                 125

Arg Gly Lys Asp Leu Gln Glu Asn Tyr Cys Arg Asn Pro Arg Gly Glu
        130                 135                 140

Glu Gly Gly Pro Trp Cys Phe Thr Ser Asn Pro Glu Val Arg Tyr Glu
145                 150                 155                 160

Val Cys Asp Ile Pro Gln Cys Ser Glu Val Glu His His His His
                165                 170                 175

His

<210> SEQ ID NO 10
<211> LENGTH: 534
<212> TYPE: DNA
<213> ORGANISM: Artificial sequence
<220> FEATURE:
<223> OTHER INFORMATION: Nucleotide sequence coding K1K1

<400> SEQUENCE: 10
atggccatta gaaactgcat cattggtaaa ggacgcagct acaagggaac agtatctatc      60
actaagagtg gcatcaaatg tcagccctgg agttccatga taccacacga acacagcttt    120 tgccttcga gctatcgggg taaagaccta caggaaaact actgtcgaaa tcctcgaggg     180
gaagaagggg gaccctggtg tttcacaagc aatccagagg tacgctacga ggtctgtgac    240
attcctcagt gttcagaagt tgaatgcatc attggtaaag gacgcagcta caagggaaca    300
gtatctatca ctaagagtgg catcaaatgt cagccctgga gttccatgat accacacgaa    360
cacagctttt gccttcgag ctatcggggt aaagacctac aggaaaacta ctgtcgaaat    420
cctcgagggg aagaaggggg accctggtgt ttcacaagca atccagaggt acgctacgag    480
gtctgtgaca ttcctcagtg tagtgaagtt gaacatcatc atcatcatca ttga         534

<210> SEQ ID NO 11
<211> LENGTH: 5683
<212> TYPE: DNA
<213> ORGANISM: Artificial sequence
<220> FEATURE:
<223> OTHER INFORMATION: Plasmid coding K1K1

<400> SEQUENCE: 11
ggccgcactc gagtctggta aagaaaccgc tgctgcgaaa tttgaacgcc agcacatgga      60
ctcgtctact agcgcagctt aattaaccta ggctgctgcc accgctgagc aataactagc    120 ataaccccctt gggcctcta acgggtcttg agggggtttt tgctgaaag gaggaactat    180 atccggattg gcgaatggga cgcgccctgt agcggcgcat taagcgcggc gggtgtggtg    240
gttacgcgca gcgtgaccgc tacacttgcc agcgccctag cgcccgctcc tttcgctttc    300
ttcccttcct ttctcgccac gttcgccggc tttccccgtc aagctctaaa tcgggggctc    360
cctttagggt tccgatttag tgctttacgg cacctcgacc ccaaaaaact tgattagggt    420
gatggttcac gtagtgggcc atcgccctga tagacggttt ttcgcccttt gacgttggag    480
tccacgttct ttaatagtgg actcttgttc caaactggaa caacactcaa ccctatctcg    540
gtctattctt ttgatttata agggattttg ccgatttcgg cctattggtt aaaaaatgag    600
ctgatttaac aaaaatttaa cgcgaatttt aacaaaatat taacgtttac aatttctggc    660
```

| | |
|---|---|
| ggcacgatgg catgagatta tcaaaaagga tcttcaccta gatcctttta aattaaaaat | 720 |
| gaagttttaa atcaatctaa agtatatatg agtaaacttg gtctgacagt taccaatgct | 780 |
| taatcagtga ggcacctatc tcagcgatct gtctatttcg ttcatccata gttgcctgac | 840 |
| tccccgtcgt gtagataact acgatacggg agggcttacc atctggcccc agtgctgcaa | 900 |
| tgataccgcg agacccacgc tcaccggctc cagatttatc agcaataaac cagccagccg | 960 |
| gaagggccga gcgcagaagt ggtcctgcaa ctttatccgc ctccatccag tctattaatt | 1020 |
| gttgccggga agctagagta agtagttcgc cagttaatag tttgcgcaac gttgttgcca | 1080 |
| ttgctacagg catcgtggtg tcacgctcgt cgtttggtat ggcttcattc agctccggtt | 1140 |
| cccaacgatc aaggcgagtt acatgatccc ccatgttgtg caaaaaagcg gttagctcct | 1200 |
| tcggtcctcc gatcgttgtc agaagtaagt tggccgcagt gttatcactc atggttatgg | 1260 |
| cagcactgca taattctctt actgtcatgc catccgtaag atgcttttct gtgactggtg | 1320 |
| agtactcaac caagtcattc tgagaatagt gtatgcggcg accgagttgc tcttgcccgg | 1380 |
| cgtcaatacg ggataatacc gcgccacata gcagaacttt aaaagtgctc atcattggaa | 1440 |
| aacgttcttc ggggcgaaaa ctctcaagga tcttaccgct gttgagatcc agttcgatgt | 1500 |
| aacccactcg tgcacccaac tgatcttcag catcttttac tttcaccagc gtttctgggt | 1560 |
| gagcaaaaac aggaaggcaa aatgccgcaa aaagggaat aagggcgaca cggaaatgtt | 1620 |
| gaatactcat actcttcctt tttcaatcat gattgaagca tttatcaggg ttattgtctc | 1680 |
| atgagcggat acatatttga atgtatttag aaaaataaac aaataggtca tgaccaaaat | 1740 |
| cccttaacgt gagttttcgt tccactgagc gtcagacccc gtagaaaaga tcaaaggatc | 1800 |
| ttcttgagat cctttttttc tgcgcgtaat ctgctgcttg caaacaaaaa aaccaccgct | 1860 |
| accagcggtg gtttgtttgc cggatcaaga gctaccaact cttttttccga aggtaactgg | 1920 |
| cttcagcaga gcgcagatac caaatactgt ccttctagtg tagccgtagt taggccacca | 1980 |
| cttcaagaac tctgtagcac cgcctacata cctcgctctg ctaatcctgt taccagtggc | 2040 |
| tgctgccagt ggcgataagt cgtgtcttac cgggttggac tcaagacgat agttaccgga | 2100 |
| taaggcgcag cggtcgggct gaacggggggg ttcgtgcaca cagcccagct tggagcgaac | 2160 |
| gacctacacc gaactgagat acctacagcg tgagctatga gaaagcgcca cgcttcccga | 2220 |
| agggagaaag gcggacaggt atccggtaag cggcagggtc ggaacaggag agcgcacgag | 2280 |
| ggagcttcca gggggaaacg cctggtatct ttatagtcct gtcgggtttc gccacctctg | 2340 |
| acttgagcgt cgatttttgt gatgctcgtc aggggggcgg agcctatgga aaaacgccag | 2400 |
| caacgcggcc ttttttacggt tcctggcctt ttgctggcct tttgctcaca tgttctttcc | 2460 |
| tgcgttatcc cctgattctg tggataaccg tattaccgcc tttgagtgag ctgataccgc | 2520 |
| tcgccgcagc cgaacgaccg agcgcagcga gtcagtgagc gaggaagcgg aagagcgcct | 2580 |
| gatgcggtat tttctcctta cgcatctgtg cggtatttca caccgcatat atggtgcact | 2640 |
| ctcagtacaa tctgctctga tgccgcatag ttaagccagt atacactccg ctatcgctac | 2700 |
| gtgactgggt catggctgcg ccccgacacc cgccaacacc cgctgacgcg ccctgacggg | 2760 |
| cttgtctgct cccggcatcc gcttacagac aagctgtgac cgtctccggg agctgcatgt | 2820 |
| gtcagaggtt ttcaccgtca tcaccgaaac gcgcgaggca gctgcggtaa agctcatcag | 2880 |
| cgtggtcgtg aagcgattca cagatgtctg cctgttcatc cgcgtccagc tcgttgagtt | 2940 |
| tctccagaag cgttaatgtc tggcttctga taaagcgggc catgttaagg gcggtttttt | 3000 |
| cctgtttggt cactgatgcc tccgtgtaag ggggatttct gttcatgggg gtaatgatac | 3060 |

```
cgatgaaacg agagaggatg ctcacgatac gggttactga tgatgaacat gcccggttac    3120
tggaacgttg tgagggtaaa caactggcgg tatggatgcg gcgggaccag agaaaaatca    3180
ctcagggtca atgccagcgc ttcgttaata cagatgtagg tgttccacag ggtagccagc    3240
agcatcctgc gatgcagatc cggaacataa tggtgcaggg cgctgacttc cgcgtttcca    3300
gactttacga aacacggaaa ccgaagacca ttcatgttgt tgctcaggtc gcagacgttt    3360
tgcagcagca gtcgcttcac gttcgctcgc gtatcggtga ttcattctgc taaccagtaa    3420
ggcaaccccg ccagcctagc cgggtcctca acgacaggag cacgatcatg ctagtcatgc    3480
cccgcgccca ccggaaggag ctgactgggt tgaaggctct caagggcatc ggtcgagatc    3540
ccggtgccta atgagtgagc taacttacat taattgcgtt gcgctcactg cccgctttcc    3600
agtcgggaaa cctgtcgtgc cagctgcatt aatgaatcgg ccaacgcgcg gggagaggcg    3660
gtttgcgtat tgggcgccag ggtggttttt cttttcacca gtgagacggg caacagctga    3720
ttgcccttca ccgcctggcc ctgagagagt tgcagcaagc ggtccacgct ggtttgcccc    3780
agcaggcgaa aatcctgttt gatggtggtt aacggcggga tataacatga gctgtcttcg    3840
gtatcgtcgt atcccactac cgagatgtcc gcaccaacgc gcagcccgga ctcggtaatg    3900
gcgcgcattg cgcccagcgc catctgatcg ttggcaacca gcatcgcagt gggaacgatg    3960
ccctcattca gcatttgcat ggtttgttga aaaccggaca tggcactcca gtcgccttcc    4020
cgttccgcta tcggctgaat ttgattgcga gtgagatatt tatgccagcc agccagacgc    4080
agacgcgccg agacagaact taatgggccc gctaacagcg cgatttgctg gtgacccaat    4140
gcgaccagat gctccacgcc cagtcgcgta ccgtcttcat gggagaaaat aatactgttg    4200
atgggtgtct ggtcagagac atcaagaaat aacgccggaa cattagtgca ggcagcttcc    4260
acagcaatgg catcctggtc atccagcgga tagttaatga tcagcccact gacgcgttgc    4320
gcgagaagat tgtgcaccgc cgctttacag gcttcgacgc cgcttcgttc taccatcgac    4380
accaccacgc tggcacccag ttgatcggcg cgagatttaa tcgccgcgac aatttgcgac    4440
ggcgcgtgca gggccagact ggaggtggca acgccaatca gcaacgactg tttgcccgcc    4500
agttgttgtg ccacgcggtt gggaatgtaa ttcagctccg ccatcgccgc ttccactttt    4560
tcccgcgttt tcgcagaaac gtggctggcc tggttcacca cgcgggaaac ggtctgataa    4620
gagacaccgg catactctgc gacatcgtat aacgttactg gtttcacatt caccaccctg    4680
aattgactct cttccgggcg ctatcatgcc ataccgcgaa aggttttgcg ccattcgatg    4740
gtgtccggga tctcgacgct ctcccttatg cgactcctgc attaggaagc agcccagtag    4800
taggttgagg ccgttgagca ccgccgccgc aaggaatggt gcatgcaagg agatggcgcc    4860
caacagtccc ccggccacgg ggcctgccac catacccacg ccgaaacaag cgctcatgag    4920
cccgaagtgg cgagcccgat cttccccatc ggtgatgtcg gcgatatagg cgccagcaac    4980
cgcacctgtg gcgccggtga tgccggccac gatgcgtccg gcgtagagga tcgagatcga    5040
tctcgatccc gcgaaattaa tacgactcac tataggggaa ttgtgagcgg ataacaattc    5100
ccctctagaa ataattttgt ttaactttaa gaaggagata taccatggcc attagaaact    5160
gcatcattgg taaaggacgc agctacaagg gaacagtatc tatcactaag agtggcatca    5220
aatgtcagcc ctggagttcc atgataccac acgaacacag cttttttgcct tcgagctatc    5280 ggggtaaaga cctacaggaa aactactgtc gaaatcctcg aggggaagaa ggggaccct    5340 ggtgtttcac aagcaatcca gaggtacgct acgaggtctg tgacattcct cagtgttcag    5400
```

-continued

```
aagttgaatg catcattggt aaaggacgca gctacaaggg aacagtatct atcactaaga     5460
gtggcatcaa atgtcagccc tggagttcca tgataccaca cgaacacagc tttttgcctt     5520
cgagctatcg gggtaaagac ctacaggaaa actactgtcg aaatcctcga ggggaagaag     5580
ggggaccctg tgtttcaca agcaatccag aggtacgcta cgaggtctgt gacattcctc      5640
agtgtagtga agttgaacat catcatcatc atcattgatg agc                       5683
```

<210> SEQ ID NO 12
<211> LENGTH: 728
<212> TYPE: PRT
<213> ORGANISM: Homo sapiens

<400> SEQUENCE: 12

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
```

His Asp Met Thr Pro Glu Asn Phe Lys Cys Lys Asp Leu Arg Glu Asn
325                 330                 335
            340                 345                 350

Tyr Cys Arg Asn Pro Asp Gly Ser Glu Ser Pro Trp Cys Phe Thr Thr
355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
            405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Ala His
            435                 440                 445

Gly Pro Trp Cys Tyr Thr Gly Asn Pro Leu Ile Pro Trp Asp Tyr Cys
450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
            485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
            515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
            565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
            595                 600                 605

Lys Thr Ser Cys Ser Val Tyr Gly Trp Gly Tyr Thr Gly Leu Ile Asn
610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
            645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
            725

<210> SEQ ID NO 13

```
<211> LENGTH: 171
<212> TYPE: PRT
<213> ORGANISM: Artificial sequence
<220> FEATURE:
<223> OTHER INFORMATION: K1K1 variant 1

<400> SEQUENCE: 13

Met Ala Ile Arg Asn Cys Ile Ile Gly Lys Gly Arg Ser Tyr Lys Gly
1               5                   10                  15

Thr Val Ser Ile Thr Lys Ser Gly Ile Lys Cys Gln Pro Trp Ser Ser
            20                  25                  30

Met Ile Pro His Glu His Ser Phe Leu Pro Ser Ser Tyr Arg Gly Lys
        35                  40                  45

Asp Leu Gln Glu Asn Tyr Cys Arg Asn Pro Arg Gly Glu Glu Gly Gly
    50                  55                  60

Pro Trp Cys Phe Thr Ser Asn Pro Glu Val Arg Tyr Glu Val Cys Asp
65                  70                  75                  80

Ile Pro Gln Cys Ser Glu Val Glu Cys Ile Ile Gly Lys Gly Arg Ser
                85                  90                  95

Tyr Lys Gly Thr Val Ser Ile Thr Lys Ser Gly Ile Lys Cys Gln Pro
            100                 105                 110

Trp Ser Ser Met Ile Pro His Glu His Ser Phe Leu Pro Ser Ser Tyr
        115                 120                 125

Arg Gly Lys Asp Leu Gln Glu Asn Tyr Cys Arg Asn Pro Arg Gly Glu
    130                 135                 140

Glu Gly Gly Pro Trp Cys Phe Thr Ser Asn Pro Glu Val Arg Tyr Glu
145                 150                 155                 160

Val Cys Asp Ile Pro Gln Cys Ser Glu Val Glu
                165                 170

<210> SEQ ID NO 14
<211> LENGTH: 183
<212> TYPE: PRT
<213> ORGANISM: Artificial sequence
<220> FEATURE:
<223> OTHER INFORMATION: K1K1 variant 2

<400> SEQUENCE: 14

Met Ala Ile Arg Asn Cys Ile Ile Gly Lys Gly Arg Ser Tyr Lys Gly
1               5                   10                  15

Thr Val Ser Ile Thr Lys Ser Gly Ile Lys Cys Gln Pro Trp Ser Ser
            20                  25                  30

Met Ile Pro His Glu His Ser Phe Leu Pro Ser Ser Tyr Arg Gly Lys
        35                  40                  45

Asp Leu Gln Glu Asn Tyr Cys Arg Asn Pro Arg Gly Glu Glu Gly Gly
    50                  55                  60

Pro Trp Cys Phe Thr Ser Asn Pro Glu Val Arg Tyr Glu Val Cys Asp
65                  70                  75                  80

Ile Pro Gln Cys Gly Gly Gly Gly Ser Leu Val Pro Arg Gly Ser Gly
                85                  90                  95

Gly Gly Gly Ser Cys Ile Ile Gly Lys Gly Arg Ser Tyr Lys Gly Thr
            100                 105                 110

Val Ser Ile Thr Lys Ser Gly Ile Lys Cys Gln Pro Trp Ser Ser Met
        115                 120                 125

Ile Pro His Glu His Ser Phe Leu Pro Ser Ser Tyr Arg Gly Lys Asp
    130                 135                 140

Leu Gln Glu Asn Tyr Cys Arg Asn Pro Arg Gly Glu Glu Gly Gly Pro
```

```
                145                 150                 155                 160
Trp Cys Phe Thr Ser Asn Pro Glu Val Arg Tyr Glu Val Cys Asp Ile
                165                 170                 175
Pro Gln Cys Ser Glu Val Glu
                180

<210> SEQ ID NO 15
<211> LENGTH: 171
<212> TYPE: PRT
<213> ORGANISM: Artificial sequence
<220> FEATURE:
<223> OTHER INFORMATION: K1K1 variant 3

<400> SEQUENCE: 15

Met Ala Ile Arg Asn Cys Ile Ile Gly Lys Gly Arg Ser Tyr Lys Gly
1               5                   10                  15

Thr Val Ser Ile Thr Lys Ser Gly Ile Lys Cys Gln Pro Trp Ser Ser
                20                  25                  30

Met Ile Pro His Glu His Ser Phe Leu Pro Ser Ser Tyr Arg Gly Lys
            35                  40                  45

Asp Leu Gln Glu Asn Tyr Cys Arg Asn Pro Arg Gly Glu Glu Gly Gly
        50                  55                  60

Pro Trp Cys Phe Thr Ser Asn Pro Glu Val Arg Tyr Glu Val Cys Asp
65                  70                  75                  80

Ile Pro Gln Cys Gly Ser Gly Gly Cys Ile Ile Gly Lys Gly Arg Ser
                85                  90                  95

Tyr Lys Gly Thr Val Ser Ile Thr Lys Ser Gly Ile Lys Cys Gln Pro
                100                 105                 110

Trp Ser Ser Met Ile Pro His Glu His Ser Phe Leu Pro Ser Ser Tyr
            115                 120                 125

Arg Gly Lys Asp Leu Gln Glu Asn Tyr Cys Arg Asn Pro Arg Gly Glu
        130                 135                 140

Glu Gly Gly Pro Trp Cys Phe Thr Ser Asn Pro Glu Val Arg Tyr Glu
145                 150                 155                 160

Val Cys Asp Ile Pro Gln Cys Ser Glu Val Glu
                165                 170

<210> SEQ ID NO 16
<211> LENGTH: 177
<212> TYPE: PRT
<213> ORGANISM: Artificial sequence
<220> FEATURE:
<223> OTHER INFORMATION: K1K1 variant 4

<400> SEQUENCE: 16

Met Ala Ile Arg Asn Cys Ile Ile Gly Glu Gly Glu Ser Tyr Lys Gly
1               5                   10                  15

Thr Val Ser Ile Thr Lys Ser Gly Ile Lys Cys Gln Pro Trp Ser Ser
                20                  25                  30

Met Ile Pro His Glu His Ser Phe Leu Pro Ser Ser Tyr Arg Gly Lys
            35                  40                  45

Asp Leu Gln Glu Asn Tyr Cys Arg Asn Pro Arg Gly Glu Glu Gly Gly
        50                  55                  60

Pro Trp Cys Phe Thr Ser Asn Pro Glu Val Arg Tyr Glu Val Cys Asp
65                  70                  75                  80

Ile Pro Gln Cys Ser Glu Val Glu Cys Ile Ile Gly Glu Gly Glu Ser
                85                  90                  95
```

Tyr Lys Gly Thr Val Ser Ile Thr Lys Ser Gly Ile Lys Cys Gln Pro
            100                 105                 110

Trp Ser Ser Met Ile Pro His Glu His Ser Phe Leu Pro Ser Ser Tyr
        115                 120                 125

Arg Gly Lys Asp Leu Gln Glu Asn Tyr Cys Arg Asn Pro Arg Gly Glu
    130                 135                 140

Glu Gly Gly Pro Trp Cys Phe Thr Ser Asn Pro Glu Val Arg Tyr Glu
145                 150                 155                 160

Val Cys Asp Ile Pro Gln Cys Ser Glu Val Glu His His His His
                165                 170                 175

His

<210> SEQ ID NO 17
<211> LENGTH: 16
<212> TYPE: PRT
<213> ORGANISM: Artificial sequence
<220> FEATURE:
<223> OTHER INFORMATION: linker

<400> SEQUENCE: 17

Gly Gly Gly Gly Ser Leu Val Pro Arg Gly Ser Gly Gly Gly Gly Ser
1               5                   10                  15

<210> SEQ ID NO 18
<211> LENGTH: 6
<212> TYPE: PRT
<213> ORGANISM: Artificial sequence
<220> FEATURE:
<223> OTHER INFORMATION: cleavage site

<400> SEQUENCE: 18

Leu Val Pro Arg Gly Ser
1               5

<210> SEQ ID NO 19
<211> LENGTH: 5
<212> TYPE: PRT
<213> ORGANISM: Artificial sequence
<220> FEATURE:
<223> OTHER INFORMATION: linker

<400> SEQUENCE: 19

Gly Ser Gly Gly Ser
1               5

<210> SEQ ID NO 20
<211> LENGTH: 22
<212> TYPE: DNA
<213> ORGANISM: Artificial sequence
<220> FEATURE:
<223> OTHER INFORMATION: primer

<400> SEQUENCE: 20
ttcaacttct gaacactgag ga                                          22

<210> SEQ ID NO 21
<211> LENGTH: 29
<212> TYPE: DNA
<213> ORGANISM: Artificial sequence
<220> FEATURE:
<223> OTHER INFORMATION: primer

<400> SEQUENCE: 21
cagaagttga atgcatcatt ggtgaagga                                   29

```
<210> SEQ ID NO 22
<211> LENGTH: 43
<212> TYPE: DNA
<213> ORGANISM: Artificial sequence
<220> FEATURE:
<223> OTHER INFORMATION: primer

<400> SEQUENCE: 22
atcatcccat ggccattaga aactgcatca ttggtaaagg acg          43

<210> SEQ ID NO 23
<211> LENGTH: 18
<212> TYPE: DNA
<213> ORGANISM: Artificial sequence
<220> FEATURE:
<223> OTHER INFORMATION: primer

<400> SEQUENCE: 23
acagcggccg ctcatcaa                                       18

<210> SEQ ID NO 24
<211> LENGTH: 20
<212> TYPE: DNA
<213> ORGANISM: Artificial sequence
<220> FEATURE:
<223> OTHER INFORMATION: primer

<400> SEQUENCE: 24
taatacgact cactataggg                                     20
```